United States Patent
Zhou et al.

(10) Patent No.: US 11,261,147 B2
(45) Date of Patent: Mar. 1, 2022

(54) PROCESS FOR PREPARING FLUOROBENZENE AND BENZOIC ACID HYPOFLUORITE

(71) Applicant: Fujian Yongjing Technology Co., Ltd, Shaowu (CN)

(72) Inventors: Changyue Zhou, Shaowu (CN); Hongjun Du, Shaowu (CN); Wenting Wu, Shaowu (CN)

(*) Notice: Subject to any disclaimer, the term of this patent is extended or adjusted under 35 U.S.C. 154(b) by 0 days.

(21) Appl. No.: 16/907,191

(22) Filed: Jun. 20, 2020

(65) Prior Publication Data

US 2021/0061736 A1    Mar. 4, 2021

(30) Foreign Application Priority Data

Aug. 27, 2019   (DE) .......................... 102019122901.4

(51) Int. Cl.
*C07C 17/363*  (2006.01)
*B01J 4/00*  (2006.01)
(Continued)

(52) U.S. Cl.
CPC ............ *C07C 17/363* (2013.01); *B01J 4/002* (2013.01); *B01J 19/0093* (2013.01); *B01J 19/2435* (2013.01); *B01J 19/32* (2013.01); *B01J 2219/00033* (2013.01); *B01J 2219/00824* (2013.01); *B01J 2219/00835* (2013.01);
(Continued)

(58) Field of Classification Search
CPC ....... C07C 17/363; C07C 25/13; C07C 71/00; C07C 51/60; B01J 19/0093; B01J 19/32; B01J 2219/00925
See application file for complete search history.

(56) References Cited

U.S. PATENT DOCUMENTS

2004/0156762 A1 *  8/2004  Schuppich ............... F28D 3/00
                                                                 422/129

FOREIGN PATENT DOCUMENTS

WO      WO-03064371 A1 *  8/2003  ............. C07C 71/00

OTHER PUBLICATIONS

Liu et al., Based-promoted silver-catalyzed protodeboronation of arylboronic acids and esters (RSC Adv., vol. 5, 15354-15358, Jan. 26, 2015).*

(Continued)

*Primary Examiner* — Jafar F Parsa

(57) ABSTRACT

The invention relates to a use of a fluorination gas, the elemental fluorine ($F_2$) is preferably present in a high concentration, e.g. in a concentration of elemental fluorine ($F_2$), especially of equal to much higher than 15% or even 20% by volume (i.e., at least 15% or even 20% by volume), and to a process for the manufacture of a fluorinated benzene starting from benzoic acid by direct fluorination employing a fluorination gas. The elemental fluorine ($F_2$) is preferably present in high concentration, and subsequent decarboxylation of the benzoic acid hypofluorite obtained by direct fluorination. The process of the invention is also directed to the manufacture of benzoic acid hypofluorite by direct fluorination of benzoic acid. Especially the invention is of interest in the preparation of fluorinatedbenzene, final products and as well intermediates, for usage in agro-, pharma-, electronics-, catalyst, solvent and other functional chemical applications.

19 Claims, 2 Drawing Sheets

(51) Int. Cl.
*B01J 19/00* (2006.01)
*B01J 19/24* (2006.01)
*B01J 19/32* (2006.01)
*C07C 25/13* (2006.01)

(52) U.S. Cl.
CPC .............. *B01J 2219/00891* (2013.01); *B01J 2219/00925* (2013.01); *B01J 2219/00959* (2013.01); *B01J 2219/00961* (2013.01); *B01J 2219/00963* (2013.01); *B01J 2219/308* (2013.01); *B01J 2219/3325* (2013.01); *C07C 25/13* (2013.01)

(56) References Cited

OTHER PUBLICATIONS

Sandrine et al., Decarboxylative fluorination of aliphatic carboxylic acids via photoredox catalysis, (Catalysis, J. Am. Chem. Soc., vol. 137, 5654-5657, Apr. 16, 2015).*

Ventre et al., "Decarboxylative Fluorination of Aliphatic Carboxylic Acids via Photoredox Catalysis", Apr. 16, 2015, ACS publications.

* cited by examiner

PROCESS FOR PREPARING FLUOROBENZENE AND BENZOIC ACID HYPOFLUORITE

BACKGROUND OF THE INVENTION

Field of the Disclosure

The invention relates to process for the manufacture or preparation of fluorinated benzene, in particular monofluorobenzene, using a fluorination gas comprising elemental fluorine ($F_2$) in a step of the said process. The process of the invention, for example, can comprise a batch or continuous manufacture or preparation of fluorinated benzene, in particular monofluorobenzene, using fluorination gas comprising elemental fluorine ($F_2$). The invention also relates to a new process for the manufacture or preparation of benzoic acid hypofluorite. Also, this latter process of the invention, for example, can comprise a batch or continuous manufacture or preparation of benzoic acid hypofluorite, using fluorination gas comprising elemental fluorine ($F_2$).

Description of Related Art

Fluorobenzene is still prepared by Balz-Schiemann, Sandmeyer or Halex Reaction. All this types of reactions deliver good yields but are not environmental friendly at all. Especially in Asia plants are closed by authorities due to environmental problems which cannot be solved by this type of chemistries. It is known that carboxylic acids can be fluorinated and photolytic decarboxylated like in *J. Am. Chem. Soc.* 2015137175654-5657 (https://doi.org/10.1021/jacs.5b02244). But the described F-source (e.g. Selectfluor) is extremely expensive and NOT commercially available in large industrial volumes needed for fluorobenzene. A huge drawback is the huge sceleton of Selectfluor carrying the F-atom, and this sceleton cannot be recycled and so far need to be incinerated. It is obvious that this described method is new but not feasible in industrial scale and regarding environmental aspects, even worse than Balz-Schiemann and Sandmeyer reactions. Also a sophisticated Ir-based photocatalyst is necessary which is another big drawback. No information about equipment is given as chemistry especially photochemistry with fluorinated compounds need very special dedicated equipment due to fluoride corrosion at all glassware already in lab but even much more important in industrial scale. The usage of cyanuric fluoride (2,4,6-trifluoro-1,3,5-triazine) like described already in early days in Synthesis 8, 487-8 (1973) is also not an industrial workable option not even for the first step to prepare fluorobenzene.

Fluorinated organic compounds in industrial scale are prepared by fluorine halogen exchange using anhydrous HF, addition of HF to olefinic double bonds, fluorinating agents like amine x nHF, electrofluorination with HF (in situ generation of $F_2$) where in latter case selectivity, scalability and missing environmental friendliness (formation of very toxic partial fluorinated compounds) often is and remains an unsolved problem. Another existing fluorination procedure is using $F_2$-gas directly. But this requires—besides availability of industrial quantities—the very skilled handling of $F_2$-gas and co-produced HF (hydrogen (H) vs. fluorine (F) exchange reaction).

Elemental fluorine ($F_2$) is a yellow compressed gas (fluorine gas, $F_2$-gas) with a pungent odor; it is a strong oxidant, reacts violently with combustible and reducing substances. Due to its strong chemical activity, and therefore, the need of equipment and containers with strong corrosion resistance to fluorine and HF, $F_2$-gas is usually mixed with nitrogen ($N_2$). In Europe, usually only mixtures of 95% N2 with only 5% $F_2$-gas are allowed to be transported, or with exemption permission only of up to 10% content of $F_2$-gas.

In Asia, a ratio up to 20% $F_2$-gas in inert gas like $N_2$ is available.

Such dilution of $F_2$-gas by inert gas like $N_2$ is necessary because of safety and reducing and/or controlling the chemical activity or reactivity of $F_2$-gas in chemical reactions. However, this dilution of $F_2$-gas by inert gas needed for the said reason of "deactivation" in industrial scale has the disadvantage that on the one side the dosing of $F_2$-gas diluted by inert gas is very challenging, and on the other side even more important as drawback, that the heat transfer in reactor equipment during chemical reactions with $F_2$-gas, as these reaction are very exothermic, is very much reduced by inert gas, and due to the diluting inert gas is resulting in reduced heat transfer, and in worst case might even cause runaways. Hence, in principle the inert gas is undesirably functioning as insulation gas.

It is known in the prior art to fluorinate deactivated benzene derivatives with a diluted fluorination gas, e.g., in Chambers et al. (Journal of Fluorine Chemistry 128 (2007) 29-33). Chambers is using as a fluorination gas containing 10% (vol.-%) elemental fluorine ($F_2$) in nitrogen ($N_2$) as inert gas, and is using solvents for the reaction, e.g., acetonitrile or formic acid reaction media. Chambers is reporting direct fluorination reactions of 1,4-disubstitutedaromatic systems bearing an electron withdrawing and releasing group, using microreactor technology. The fluorinated products are obtained by a process consistent with an electrophilic substitution process due to the solvents used. Thus, high selectivity and yields of monofluorinated products are reported by Chambers when using either acetonitrile or formic acid reaction media. It is known in the prior art that high relative permittivity solvents or protonic acids can be used very effectively for the fluorination of aromatic systems because, in these media, the fluorine molecule is rendered more susceptible towards nucleophilic attack by interaction with the solvent while competing free radical processes are minimized. However, in the process described by Chambers, typically, reactions are carried out only in small scale reactions, for example over a 16 h period enabling 5 to 10 g of crude product to be collected.

Also, Chambers tested in the same experimental setting as described here above, the direct fluorination of aromatic rings bearing two strong electron withdrawing groups, which aromatic rings are, of course, relatively unreactive towards electrophilic attack. However, reactions between such substrates and elemental fluorine ($F_2$), i.e., using the fluorination gas containing 10% (vol.-%) elemental fluorine ($F_2$) in nitrogen ($N_2$) as inert gas, and using a microreactor gave low conversions to fluorinated products, but in very selective, clean reactions. Nevertheless, also in this process described by Chambers, typically, reactions are carried out only in small scale reactions, for example over a 16 h period enabling 5 to 10 g of crude product to be collected. Importantly, it must be noted that despite the successful conversions in the range of 78% to 91% of fluorination reactions on deactivated benzene derivatives with a diluted fluorination gas in acetonitrile as solvent, nevertheless Chambers did not test nor motivate for testing of non-deactivated benzene itself, neither in small-scale of 5 to 10 g product quantities nor in large-scale at all.

Accordingly, there is a high demand of enabling large-scale and/or industrial production of fluorinated benzene involving a step of direct fluorination in a controlled and effective manner in a large-scale and/or industrial setting. Here, it is also an object of the invention to provide a new process for enabling the manufacture or preparation of benzoic acid hypofluorite in a controlled and effective manner, preferably in a large-scale and/or industrial setting. Another object of the present invention is to provide the said benzoic acid hypofluorite as a starting material for the manufacture or preparation of fluorinated benzene, preferably in a large-scale and/or industrial setting.

When producing fluorinated benzene in a two-step procedure by first directly fluorinating benzoic acid in a controlled and effective manner, and then subsequently in the second step decarboxylating the benzoic acid hypofluorite obtained in the fluorination step, in another aspect it is also desired to minimize, or even to substantially avoid, the dilution of the elemental fluorine ($F_2$) by inert gas, e.g. by nitrogen ($N_2$) as inert gas, and at least to enable the use of fluorination gas containing essentially higher concentrated elemental fluorine ($F_2$) than those concentrations described above and used in the prior art, e.g., essentially higher concentrated elemental fluorine ($F_2$) than 10% by volume as used by Chambers or available under exemption in Europe, or essentially higher concentrated elemental fluorine ($F_2$) than 20% by volume as available in Asia.

It is an object of the present invention to provide a high efficient process for the manufacture or for preparation of a fluorinated benzene, in particular monofluorobenzene, involving a step of direct fluorination, e.g., directly fluorinating benzoic acid, using fluorine gas ($F_2$), preferably wherein in the fluorination process a fluorine gas (fluorination gas) with concentrations of substantially more than, in particular very much higher than 15 or even 20% by volume of elemental fluorine ($F_2$), especially of equal to much higher than 25% by volume (i.e., at least 25% by volume) of elemental fluorine ($F_2$), preferably of equal to much higher than 35 or even 45% by volume of elemental fluorine ($F_2$), can be used for chemical synthesis, especially for the manufacture or for preparation of fluorobenzene compounds, in particular fluorobenzene (monofluorobenzene), as final products and/or intermediates, for usage in agro-, pharma-, electronics-, catalyst, solvent and other functional chemical applications.

It is preferably an object of the present invention to provide a fluorination process for the manufacture or preparation of a fluorinated benzene, in particular monofluorobenzene, involving a step of direct fluorination, e.g., directly fluorinating benzoic acid, using fluorine gas ($F_2$), by which it is possible to perform chemistry with a fluorination gas consisting essentially of $F_2$-gas as it directly comes out of the $F_2$-electrolysis reactors (fluorine cells), optionally only diluted for a minor degree, e.g., for adapting and controlling the fluorination process and its parameters.

It is preferably another object of the present invention to provide a fluorination process for the manufacture or preparation of a fluorinated benzene, in particular monofluorobenzene, involving a step of direct fluorination, e.g., directly fluorinating benzoic acid, using fluorine gas ($F_2$-gas), by means of special equipment and special reactor design.

It is preferably still another object of the present invention to provide a fluorination process for the manufacture or preparation of a fluorinated benzene, in particular monofluorobenzene, involving a step of direct fluorination, e.g., directly fluorinating benzoic acid, using fluorine gas ($F_2$-gas), wherein the process can be performed in a large-scale and/or industrial production of fluorinated benzene.

SUMMARY OF THE INVENTION

The objects of the invention are solved as defined in the claims, and described herein after in detail.

The invention relates to a use of a fluorination gas, wherein the elemental fluorine ($F_2$) is preferably present in a high concentration, for example, in a concentration of elemental fluorine ($F_2$), especially of equal to much higher than 15% or even 20% by volume (i.e., at least 15% or even 20% by volume), and to a process for the manufacture of a fluorinated benzene starting from benzoic acid involving a step of direct fluorination employing a fluorination gas, wherein the elemental fluorine ($F_2$) is preferably present in a high concentration, and subsequent decarboxylation of the benzoic acid hypofluorite obtained by direct fluorination. The process of the invention is also directed to the manufacture of a benzoic acid hypofluorite by direct fluorination of benzoic acid. Especially the invention is of interest in the preparation of benzoic acid hypofluorite, and/or subsequently fluorinated benzene, final products and as well intermediates, for usage in agro-, pharma-, electronics-, catalyst, solvent and other functional chemical applications. The fluorination process of the invention may be performed batch-wise or in a continuous manner. If the process of the invention is performed batch-wise, a column (tower) reactor may be used. If the process of the invention is continuous a microreactor may be used. The invention is characterized in that the starting compound is benzoic acid, and the fluorinated compound produced is a benzoic acid hypofluorite obtained by direct fluorination, which benzoic acid hypofluorite can be converted by decarboxylation to a fluorinated benzene, preferably monofluorobenzene.

The inventive process disclosed hereunder delivers fluorobenzene in high yield in environmental friendly and economic feasible manner involving a step of a direct fluorination of benzoic acid with $F_2$-gas to obtain the corresponding benzoic acid hypofluorite (hypofluorusbenzoic acid) followed by a decarboxylation step to obtain a fluorinated benzene, preferably monofluorobenzene. The general two step reaction sequence is given hereunder.

Scheme 1: First step (direct fluorination).

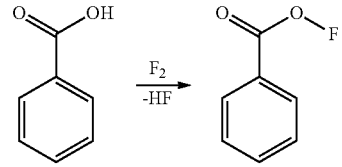

Scheme 2: Second step (decarboxylation).

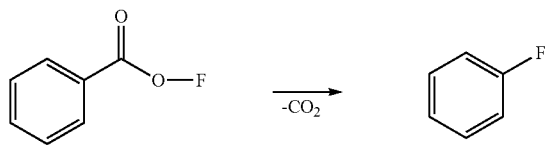

The decarboxylation step to obtain a fluorinated benzene, preferably monofluorobenzene, by decarboxylation of benzoic acid hypofluorite can be performed by several options. For example, the decarboxylation may be performed by thermal decarboxylation or photochemical decarboxylation. According to the invention a photochemical decarboxylation is preferred. A photochemical decarboxylation, for example, can be performed either by direct irradiation ($\lambda$>180 nm, option 1), or in presence of a photosensitizer also is also workable (light initiated, option 2).

Scheme 3: Option 1 for photochemical decarboxylation.

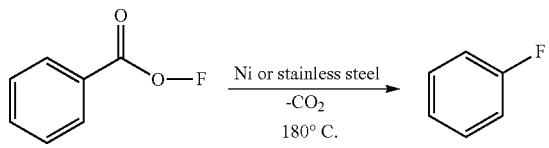

A photochemical decarboxylation either by direct irradiation ($\lambda$>180 nm=option 1) or in presence of a photosensitizer also is also workable (light initiated=option 2) and inventive, the reaction is induced by wavelength $\lambda$>180 nm (remark: but 254 nm is the strongest short wave length line of a Hg-lamp), light can be produced by different light sources like Hg-medium or Hg-high pressure lamps, Phillips tube lamps or even LEDs. Pre-tests were made in a so called Rayonet Photochemical Reactor RPR-100" (supplier: "The Southern New England Ultraviolet Company") with 254 nm tubes. For industrial scale, immersed shaft photolysis reactors are still the preferred ones as they use only 1 Hg-lamp in the middle surrounded by product mixtures which have to be irradiated. LED reactors for reactions which need higher power are economically still less preferred as the construction of 1000s of copper cables into a system is necessary.

Advantage of a photochemical induced decarboxylation is the lower useable temperature vs. the quite high temperature needed for the thermal decarboxylation. Photocatalyzed Decarboxylation and reactions of carboxylic acid hypobromide is described e.g. by Candish, L.; et al, Chemical Science (2017), 8(5), 3618-3622

(https://pubs.rsc.org/en/content/articlelanding/2017/SC/C6SC05533H#!divAbstract) but this procedure is not industrial suitable and not economic due to high cost of the photocatalyst and too low selectivities for the described products.

Scheme 4: Option 2 for photochemical decarboxylation.

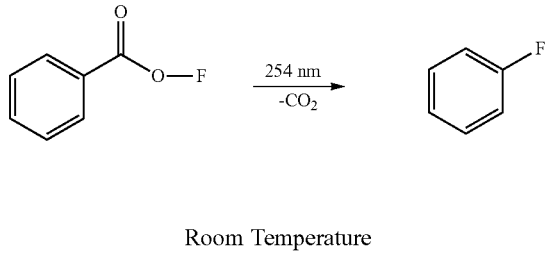

Room Temperature

As traces of fluoride will already damage photoreactors made out of glassware, any glassware and glass windows (e.g. if LEDs are used) need to be protected by a plastics coating, especially necessary for industrial scale.

Some potential transparent plastics are, for example (see in https://www.interempresas.net/Plastico/Articulos/5544-La-transparencia-en-los-plasticos.html):

the ETFE, with a 95% light transmission
polimethyl methacrylate, with a rate of 92 percent;
the polystyrene, with an index equal to or greater than 90%;
the polycarbonate, ranging from 80% to 90%;
the cellulose, with rates of the order of 85 percent;
acrylo-styrene-butadiene, the amorphous polyamides, UP resins, epoxys and phenolic and some other plastic f.
Optical Properties of Transparent Polymers
See, for example in: https://omnexus.specialchem.com/tech-library/article/comprehensive-list-of-transparent-polymers.

|  | Transmission [%] | Refractive Index | Haze [%] |
| --- | --- | --- | --- |
| PC | 86-91 | 1.584-1.586 | 0.2-2.7 |
| PMMA | 89-92 | 1.49 | 0.10-2.6 |
| PET | 87-92.1 | 1.575 | 0.20-5.1 |
| PETG | 92 | 1.55 | 0.7 |
| Clear PVC | Upto 97% | 1.381 | 2.5 |
| LSR | 94 | 1.41 | <1 |
| COC | 91 | 1.53 | 3 |
| LDPE | 4.4-94 | 1.476 | 3-12 |
| Ionomer Resin | 93.4 | 1.49 | 2.7-4.2 |
| Transparent PP | — | 1.347 | — |
| FEP | 92 | 1.55 | 0.7 |
| SMMA | 89-92.8 | 1.59 | 0.3-1.0 |
| SAN | 86.2-89.3 | 1.57 | 0.4-2.8 |
| GPPS | 88-90 | 1.6 | 0.3-1.1 |
| Transparent ABS | 86 | 1.52 | 3 |

Another source for transparent plastics: https://www.ultrapolymers.com/sites/default/files/421049-Transparent-Plastics-LR.pdf The most suitable plastics is FEP or alternatively polycarbonate which is used as a kind of shrinking pipe over the photoreactor or as a foil type for covering glass windows. Fluorinated ethylene propylene (FEP) is a copolymer of hexafluoropropylene and tetrafluoroethylene. It differs from the polytetrafluoroethylene (PTFE) resins in that it is melt-processable using conventional injection molding and screw extrusion techniques.

According to the objects, the present invention provides a high efficient process for the manufacture or for preparation of a fluorinated benzene, in particular monofluorobenzene, involving a step of direct fluorination using fluorine gas ($F_2$), e.g., a step of fluorinating benzoic acid to obtain benzoic acid hypofluorite, wherein preferably in the fluorination process a fluorine gas (fluorination gas) with concentrations of substantially more than, in particular very much higher than 15% by volume or in particular than 20% by volume of elemental fluorine ($F_2$), especially of equal to much higher than 25% by volume (i.e., at least 25% by volume) of elemental fluorine ($F_2$), preferably of equal to much higher than 35% by volume or in particular than 45% by volume of elemental fluorine ($F_2$), is used for chemical synthesis, especially for the manufacture or for preparation of benzoic acid hypofluorite, and/or subsequently fluorinated benzene, in particular monofluorobenzene, as final products and/or intermediates, for usage in agro-, pharma-, electronics-, catalyst, solvent and other functional chemical applications.

Preferably, the present invention provides a fluorination process for the manufacture or preparation of a fluorinated benzene, in particular monofluorobenzene, involving a step of direct fluorination using fluorine gas ($F_2$), e.g., a step of fluorinating benzoic acid to obtain benzoic acid hypofluorite, by which it is possible to perform chemistry with $F_2$ as it comes directly out of the $F_2$-electrolysis reactors (fluorine cells).

More preferably, the present invention provides a fluorination process for the manufacture or preparation of a fluorinated benzene, in particular monofluorobenzene, involving a step of direct fluorination using fluorine gas ($F_2$), e.g., a step of fluorinating benzoic acid to obtain benzoic acid hypofluorite, by means of special equipment and special reactor design, for example, as described in FIG. 1 and FIG. 2 hereunder. The special equipment and special reactor design employed by the invention may comprise one or more packed bed towers, e.g., in the form of a gas scrubber system, or one or more microreactors. A packed bed towers, e.g., in the form of a gas scrubber system, may be preferred, more preferably a packed bed towers, e.g., in the form of an inverse gas scrubber system, used in a batch process as reactor.

The fluorination process for the manufacture or preparation of a fluorinated benzene, in particular monofluorobenzene, involving a step of direct fluorination using fluorine gas ($F_2$), e.g., a step of fluorinating benzoic acid to obtain benzoic acid hypofluorite, can be performed at suitable pressures, for examples at a pressure in the range of about 1 to about 10 bar (absolute), preferably at a pressure in a range of about 1 to about 6 bar (absolute), and more preferably at a pressure in a range of about 4 to about 6 bar (absolute). In an example, the process is performed at a pressure of about 6 bar (absolute).

In the decarboxylation reaction, the pressure may, according to pressure conditions commonly used in in the technical field, and be in a range of about 1 to about 20 bar (absolute). For example, if the decarboxylation is carried out in an autoclave, the pressure can be 20 bar (absolute), and if the decarboxylation is carried out in a microreactor, pressure will be in a range of about 1 bar (absolute) to 3 bar (absolute), for example at a pressure of about 2 bar (absolute).

The fluorination process for the manufacture or preparation of a fluorinated benzene, in particular monofluorobenzene, involving a step of direct fluorination using fluorine gas ($F_2$), e.g., a step of fluorinating benzoic acid to obtain benzoic acid hypofluorite, can be performed at an approximately equimolar ratio of benzoic acid as the starting compound to the fluorination gas comprising elemental fluorine ($F_2$), optionally of highly concentrated $F_2$-gas. Preferably, the reaction is performed with a slight molar excess amount of the fluorination gas comprising elemental fluorine ($F_2$), optionally of highly concentrated $F_2$-gas.

Further, it has been discovered that despite the exothermic character of the direct fluorination reaction, involving a step of direct fluorination using fluorine gas ($F_2$), e.g., a step of fluorinating benzoic acid to obtain benzoic acid hypofluorite, e.g., within a given time period (e.g., less than 10 hours, or even less than 5 hours), the reaction of the invention can be performed as a larger scale reaction with high conversion rates, and without major impurities in the resulting fluorinated product. The fluorinated product can be produced in kilogram scale quantities, e.g., the direct fluorination process of the invention can be performed in a large-scale and/or industrial production of fluorinated benzene involving a step of direct fluorination using fluorine gas ($F_2$), e.g., a step of fluorinating benzoic acid to obtain benzoic acid hypofluorite.

As a first reference for scale orientation, and for reason of calculating quantities, reference is made to the molecular weight of benzene of 78.114 g/mol, and of monofluorobenzene of 96.10 g/mol. For reason of adapting and/or controlling process parameters, here the boiling point of benzene of about 80° C., and that of monofluorobenzene of about 85° C. are also given, each for ambient pressure.

As a second reference for scale orientation, and for reason of calculating quantities, reference is made to the molecular weight of benzoic acid of 122.123 g/mol, and of benzoic acid hypofluorite of 140.11 g/mol. For reason of adapting and/or controlling process parameters, here the melting point of about 122° C. and boiling point of about 250° C. of benzoic acid. Each of said ° C. value is for ambient pressure.

Accordingly, it is preferred that the direct fluorination process of the invention is performed in a large-scale and/or industrial production of fluorinated benzene (preferably monofluorobenzene), or of benzoic acid hypofluorite, respectively, involving a step of direct fluorination using fluorine gas ($F_2$), e.g., a step of fluorinating benzoic acid to obtain benzoic acid hypofluorite, e.g., in kilogram scale quantities, wherein in a batch process, or optionally in a continuous process, in a column reactor as described herein, at least about 1 kg of benzoic acid as the starting material is fluorinated per hour, preferably at least about 1.5 kg of benzoic acid as the starting material is fluorinated per hour, to yield benzoic acid hypofluorite, and/or subsequently a fluorinated benzene, preferably monofluorobenzene, with a conversion of at least 80%, in particular of at least 85%, preferably about at least 90%, more preferably about at least 95% conversion.

Accordingly, it is preferred that the direct fluorination process of the invention is performed in a large-scale and/or industrial production of fluorinated benzene, or of benzoic acid hypofluorite, respectively, involving a step of direct fluorination using fluorine gas ($F_2$), e.g., a step of fluorinating benzoic acid to obtain benzoic acid hypofluorite, e.g., in a larger scale or even kilogram scale quantities, wherein in a microreactor process, in a continuous process, as described herein, at least about 0.5 mol/h benzoic acid (about 61 g/h benzoic acid), or at least about 1 mol/h benzoic acid (about 122 g/h benzoic acid), preferably at least about 1.5 mol/h benzoic acid (about 183 g/h benzoic acid), more preferably at least about 2 mol/h or about 3 mol/h benzoic acid (about 244 g/h or about 366 g/h benzoic acid), as the starting material is fluorinated for a desired period of time (e.g., of at least 0.5 h, preferably of at least 1 h, more preferably of at least 2, 3, or 4 h) to produce the required large-scale and/or industrial scale quantity of benzoic acid hypofluorite, and/or subsequently fluorinated benzene (preferably monofluorobenzene), with a conversion of at least 80%, in particular of at least 85%, preferably about at least 90%, more preferably about at least 95% conversion.

The reaction is performed with an equimolar amount of $F_2$-gas, optionally of highly concentrated $F_2$-gas, as each defined herein, and preferably in a slight molar excess amount of about 0.1 to about 0.8 mol/h or of about 0.1 to about 0.5 mol/h, preferably of about 0.1 to about 0.4 mol/h or about 0.1 to about 0.3 mol/h, more preferably of about 0.1 to about 0.2 mol/h, most preferably of about 0.15 mol/h, of $F_2$-gas, optionally of highly concentrated $F_2$-gas, as each defined herein.

In a particular embodiment, it is preferred that the direct fluorination process of the invention is performed in a large-scale and/or industrial production of fluorinated benzene, or of benzoic acid hypofluorite, respectively, involving a step of direct fluorination using fluorine gas ($F_2$), e.g., a step of fluorinating benzoic acid to obtain benzoic acid hypofluorite, e.g., in kilogram scale quantities, wherein in a microreactor process, in a continuous process, as described herein, at least about 0.8 mol/h benzoic acid (about 100 g/h benzoic acid) as the starting material is fluorinated for a desired period of time of at least about 1 h or about 2 h or about 3 h or about 4 h, preferably of at least about 4.5 h or 5 h, more preferably of at least about 6 h, about 10 h, about 12 h or about 24 h, to produce the required large-scale and/or industrial scale quantity of fluorinated benzene (preferably monofluorobenzene), or of benzoic acid hypofluorite, respectively, with a conversion of at least 80%, in particular of at least 85%, preferably about at least 90%, more preferably about at least 95% conversion. Hence, in the said direct fluorination process of the invention performed in a large-scale and/or industrial production of fluorinated benzene (preferably monofluorobenzene), involving a step of direct fluorination using fluorine gas ($F_2$), e.g., a step of fluorinating benzoic acid to obtain benzoic acid hypofluorite, in a microreactor in a continuous process within the said time periods, e.g., wherein approximate kilogram scale quantities of benzoic acid of at least about 0.1 kg or about 0.2 kg or about 0.3 kg or about 0.4 kg or about 0.5 kg, or of at least about 1 kg, preferably of at least about 1.5 kg or about 1.75 kg, more preferably of at least about 2.0 kg, 2.5 kg, 3.5 kg or 5 kg, to produce the required large-scale and/or industrial scale quantity of fluorinated benzene (preferably monofluorobenzene), or of benzoic acid hypofluorite, respectively, with a conversion of at least 80%, in particular of at least 85%, preferably about at least 90%, more preferably about at least 95% conversion. The reaction is performed with an equimolar amount of $F_2$-gas, optionally of highly concentrated $F_2$-gas, and preferably in a molar amount of a slight excess of about 0.1 to about 0.8 mol/h or of about 0.1 to about 0.5 mol/h, preferably of about 0.1 to about 0.4 mol/h or about 0.1 to about 0.3 mol/h, more preferably of about 0.1 to about 0.2 mol/h, most preferably of about 0.15 mol/h, of $F_2$-gas, optionally of highly concentrated $F_2$-gas, as each defined herein.

The invention also relates to a use of a fluorination gas, preferably wherein elemental fluorine ($F_2$) is present in a high concentration of substantially more than, in particular very much more than 15% by volume or in particular than 20% by volume, preferably equal to or more than 25% by volume (vol.-%), for the manufacture of a fluorinated benzene), or of benzoic acid hypofluorite, respectively, in a liquid medium comprising or consisting of benzoic acid as starting compound, preferably wherein the elemental fluorine ($F_2$) is present in the fluorine containing gas in a high concentration in a range of from substantially more than, in particular very much more than 15 or 20 by volume (vol.-%) and up to 100% by volume, preferably equal to or more than 25 by volume (vol.-%) and up to 100% by volume (vol.-%); characterized in that the starting compound is benzoic acid, and the fluorinated compound produced is benzoic acid hypofluorite, and/or subsequently a fluorinated benzene, preferably monofluorobenzene.

It is noted that the fluorination reaction of the present invention, in particular when carried out in the specific and/or preferred equipment or reactor designs as described by the present invention herein, can be already performed with concentrations of elemental fluorine ($F_2$) of 15% by volume or in particular than 20% by volume.

However, it is preferred that the fluorination reaction of the present invention, also when carried out in the specific and/or preferred equipment or reactor designs as described by the present invention herein, is performed with concentrations of elemental fluorine ($F_2$) at least 25% by volume, and more preferably with concentrations of elemental fluorine ($F_2$) of substantially more than 35% by volume or in particular substantially more than 45% by volume of elemental fluorine ($F_2$).

According to the present invention it is particularly preferred to perform the fluorination process for the manufacture or preparation of a fluorinated benzene, in particular monofluorobenzene, involving a step of direct fluorination, e.g., a step of fluorinating benzoic acid to obtain benzoic acid hypofluorite, using fluorine gas ($F_2$), which comes directly out of the $F_2$-electrolysis reactors (fluorine cells). Such electrolysis fluorine gas ($F_2$) normally has a concentration of about 97% elemental fluorine ($F_2$).

The electrolysis fluorine gas ($F_2$) normally having a concentration of about 97% elemental fluorine ($F_2$) can be used without purification as it is derived from the $F_2$-electrolysis reactors (fluorine cells), or if desired, it may be purified.

Further, the electrolysis fluorine gas ($F_2$) normally having a concentration of about 97% by volume (vol.-%) of elemental fluorine ($F_2$) can be used in the in the such concentration as it is derived from the $F_2$-electrolysis reactors (fluorine cells), or optionally it may be diluted by an inert gas, preferably nitrogen ($N_2$), to a desired concentration of at least 80% by volume (vol.-%) of elemental fluorine ($F_2$). More preferably the electrolysis fluorine gas ($F_2$) is only diluted, if desired, by no more than 15% by volume (vol.-%), no more than 10% by volume (vol.-%), and most preferably by no more that 5% by volume (vol.-%), of an inert gas, preferably nitrogen ($N_2$).

Surprisingly it was also found that the use of inert gas in larger ratios of inert gas to elemental fluorine has disadvantages in terms of process controllability of the fluorination reaction, for example, in terms of effective mixing of the elemental fluorine with the liquid compound to be fluorinated, heat transfer control, e.g., poor heat exchange, and maintenance of desired reaction conditions in the microenvironments in the reaction mixture. These disadvantages equally apply in bed tower reactor (gas scrubber system) technology and in microbubble microreactor or comparable continuous flow technology. For example, in a coil reactor or microreactor, at high inert gas concentrations, e.g., low fluorine ($F_2$) concentrations, in addition to the poor heat exchange, there are also ineffective (reaction) zones with (inert) gas bubbles, which nullifies the advantages of using a coil reactor or a microreactor, and the same is observed in bed tower reactor (gas scrubber system) technology.

Definitions

Direct Fluorination: Introducing one or more fluorine atoms into a compound by chemically reacting a starting compound, e.g., according to the present invention benzoic acid, with elemental fluorine ($F_2$) such that one or more fluorine atoms are covalently bound into the fluorinated product compound produced, which in case of the present invention is benzoic acid hypofluorite.

Compound: A molecule composed of at least two atoms bound by covalent binding. In the molecule, often also called substance, the atoms are covalently linked together to form a self-contained, chemical formation. A molecule defined in this way is the smallest particle of a certain pure substance and has a determinable molecular mass, wherein the atoms are held together by chemical bonds and are at least as long stable that they can be observed, for example, at least spectroscopically. A molecule or substance defined in this way is the smallest part of a certain pure substance and has a determinable molecular mass, and other determinable physiochemical properties. Here, in the invention, the starting compound is benzoic acid provided to be reacted with elemental fluorine ($F_2$), and the compound produced, in a first step is benzoic acid hypofluorite, which in a second step is decarboxylated to yield fluorobenzene, e.g., monofluorobenzene.

The term "liquid medium" may mean a solvent which inert to fluorination under the reaction conditions of the direct fluorination, in which the starting compound and/or fluorinated target compound may be dissolved, and/or the starting compound itself may be a liquid serving itself as liquid medium, and in which the fluorinated target compound may be dissolved if it is not a liquid, or if it is a liquid may also serve as the liquid medium.

In the present invention, if the starting compound or the resulting product compound is a solid, then the liquid medium is provided by means of a solvent, especially, e.g. in case of a direct fluorination, the solvent is at least more resistant to elemental fluorine ($F_2$) and hydrogen fluoride (HF) than the starting compound in the direct fluorination reaction. A suitable (organic) solvent in the present invention, for example but not limiting, is acetonitrile. The direct fluorination reaction, and/or the decarboxylation reaction, of the present invention can also be carried out in water, if the solid starting compound is soluble in water ($H_2O$).

The numerical ranges disclosed herein include all values from, and including, the lower and upper value. For ranges containing explicit values (e.g., 1 to 7), any subrange between any two explicit values is included (e.g., 1 to 2; 2 to 6; 5 to 7; 3 to 7; 5 to 6; etc.).

The terms "comprising," "including," "having," and their derivatives, are not intended to exclude the presence of any additional component, step or procedure, whether or not the same is specifically disclosed. In order to avoid any doubt, all compositions claimed through use of the term "comprising" may include any additional additive, adjuvant, or compound, whether polymeric or otherwise, unless stated to the contrary. In contrast, the term, "consisting essentially of" excludes from the scope of any succeeding recitation any other component, step, or procedure, excepting those that are not essential to operability. The term "consisting of" excludes any component, step, or procedure not specifically delineated or listed. The term "or," unless stated otherwise, refers to the listed members individually as well as in any combination. Use of the singular includes use of the plural and vice versa.

The term "vol.-%" as used herein means "% by volume". Unless otherwise stated, all percentages (%) as used herein denote "vol.-%" or "% by volume", respectively.

For example, the use of the term "essentially", in referring to a fluorination gas consisting essentially of $F_2$-gas as it directly comes out of the $F_2$-electrolysis reactors (fluorine cells), means that providing such $F_2$-gas does not involve major purification and/or providing another gas, e.g., an inert gas, separate and/or in admixture in amounts and/or under conditions that would be sufficient to provide a change in the composition of an $F_2$-gas as produced in and as it is withdrawn as gaseous product from $F_2$-electrolysis reactors (fluorine cells) of more than about ±5% by volume, or preferably of more than about ±3% by volume. Accordingly, such a fluorination gas consisting essentially of $F_2$-gas as it directly comes out of the $F_2$-electrolysis reactors (fluorine cells) is meant to comprise elemental fluorine ($F_2$) in a concentration of at least about 92% by volume, or preferably of at least about 95% by volume. Especially, such a fluorination gas consisting essentially of $F_2$-gas as it directly comes out of the $F_2$-electrolysis reactors (fluorine cells) may comprise elemental fluorine ($F_2$) in a concentration in a range of about 92-100% by volume, or preferably in a range of about 95-100% by volume, or more preferably in a range of in a range of about 92-99% by volume, or preferably in a range of about 95-99% by volume, or in a range of in a range of about 92 to about 97% by volume, or preferably in a range of about 95 to about 97% by volume.

Any pressure value or range of pressure values given herein in, i.e., "bar", unless otherwise stated refer to "bar absolute".

The numerical ranges disclosed herein include all values from, and including, the lower and upper value. For ranges containing explicit values (e.g., 1 to 7), any subrange between any two explicit values is included (e.g., 1 to 2; 2 to 6; 5 to 7; 3 to 7; 5 to 6; etc.).

DESCRIPTION OF THE PREFERRED EMBODIMENTS

Figure 1:
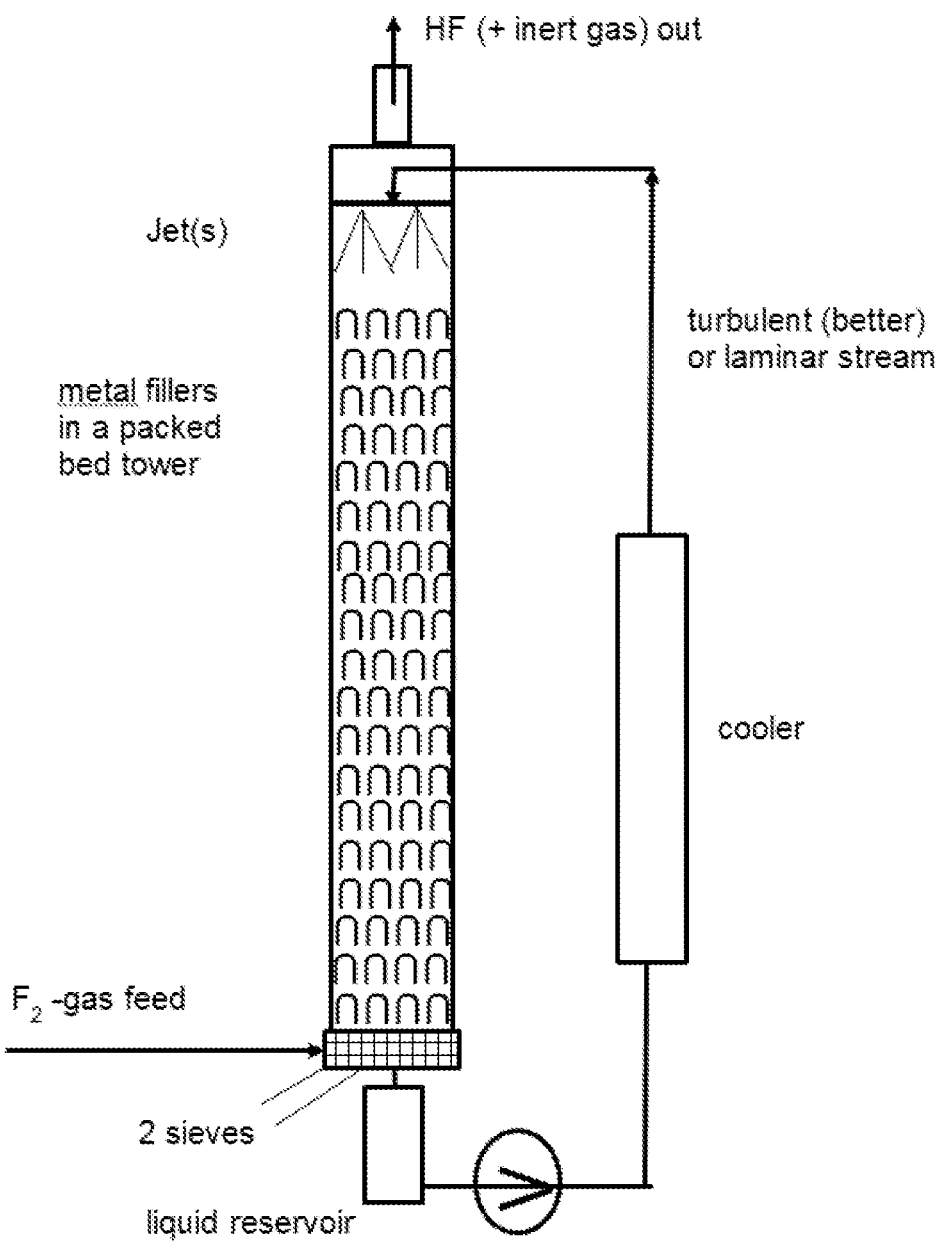
FIG. 1 shows fluorination using a gas scrubber system.

As briefly described in the Summary of the Invention, and defined in the claims and further detailed by the following description and examples herein, in a first reaction step, the invention is particularly making use of a fluorination gas, preferably wherein the elemental fluorine ($F_2$) is present in a high concentration, and to a process for the manufacture of a fluorinated benzene, preferably monofluorobenzene, involving a step of direct fluorination, e.g., a step of fluorinating benzoic acid to obtain benzoic acid hypofluorite, employing a fluorination gas, preferably wherein the elemental fluorine ($F_2$) is present in a high concentration. Herein, the invention also relates to a new process for the manufacture or preparation of benzoic acid hypofluorite. Especially, this process for the manufacture or preparation of benzoic acid hypofluorite may represent the first reaction step in the process for the manufacture of a fluorinated benzene, preferably monofluorobenzene, wherein in said first reaction step, benzoic acid is subjected to a direct fluorination employing a fluorination gas, preferably, wherein the elemental fluorine ($F_2$) is present in a high concentration.

The invention makes use of a fluorination gas, preferably wherein the elemental fluorine ($F_2$) is present in a high concentration, for example, in a concentration of elemental fluorine ($F_2$) especially of equal to much higher than 15% or 20% by volume (i.e., at least 15% or 20% by volume), and preferably at least 25% by volume, to a process for the manufacture of a fluorinated benzene, preferably monofluorobenzene, involving a step of direct fluorination using fluorine gas ($F_2$), e.g., a step of fluorinating benzoic acid to obtain benzoic acid hypofluorite, employing a fluorination gas, preferably wherein the elemental fluorine ($F_2$) is present in a high concentration. The process of the invention is directed to the manufacture of a fluorinated benzene, preferably monofluorobenzene, involving a step of direct fluorination using fluorine gas ($F_2$), e.g., a step of fluorinating benzoic acid to obtain benzoic acid hypofluorite, especially is of interest in the manufacture or preparation of fluorobenzene, in particular monofluorobenzene, as final products and as well intermediates, for usage in agro-, pharma-, electronics-, catalyst, solvent and other functional chemical applications. The fluorination process of the invention, e.g., the step of fluorinating benzoic acid to obtain benzoic acid hypofluorite, may be performed batch-wise or in a continuous manner. If the process of the invention, e.g., the step of fluorinating benzoic acid to obtain benzoic acid hypofluorite, is performed batch-wise, a column (tower) reactor may be used. If the process of the invention is continuous a microreactor may be used. If desired, it is also possible to perform the process of the invention continuously in a column (tower) reactor (gas scrubber system). However, it is preferred to perform a continuous process of the invention, e.g., a step of fluorinating benzoic acid to obtain benzoic acid hypofluorite, in a microreactor.

Especially, in one aspect the invention is directed to the use of a fluorination gas, preferably wherein elemental fluorine ($F_2$) is present in a high concentration of substantially more than, in particular very much more than at least 10% by volume of elemental fluorine ($F_2$), especially of equal to much higher than 15% or 20% by volume (i.e., at least 15% or 20% by volume), and preferably at least 25% by volume, for the manufacture of benzoic acid hypofluorite, and/or subsequently a fluorinated benzene, preferably monofluorobenzene, in a liquid medium comprising or consisting of benzoic acid as a starting compound, preferably wherein the fluorine ($F_2$) is present in the fluorine containing gas in a high concentration in a range of from substantially more than, in particular very much more than 15% or 20% by volume (i.e., at least 15% or 20% by volume), and preferably at least 20% by volume, each up to 100% by volume, preferably equal to or more than 25% by volume and up to 100% by volume (vol.-%).

In this invention it now was found that, preferably in special equipment and with special reactor design such as, e.g., a microreactor or a packed bed tower (preferably made of Hastelloy), especially a packed bed tower containing fillers, e.g., metal fillers (e.g. Hastelloy) or plastic fillers, preferably wherein the tower (e.g., made out of Hastelloy) is filled either with E-TFE or metal fillings (Hastelloy), for example each of about 10 mm diameter as available from Raschig (http://www.raschig.de/Fllkrper). The type of fillings is quite flexible, Raschigs Pall-Rings made out of Hastelloy can be used, and advantageously E-TFE-fillings.

In the said special equipment and with special reactor design such as, e.g., a microreactor or a packed bed tower (preferably made of Hastelloy), a fluorine gas with concentrations of substantially more than, in particular very much higher than 15% or 20% by volume of elemental fluorine ($F_2$), especially of equal to much higher than 20% by volume (i.e., at least 20% by volume) of elemental fluorine ($F_2$), preferably of equal to much higher than 25% by volume of elemental fluorine ($F_2$), can be used for chemical synthesis especially for the preparation of benzoic acid hypofluorite, and/or subsequently a fluorinated benzene (final products and/or intermediates) for usage in agro-, pharma-, electronics-, catalyst, solvent and other functional chemical applications. This invention allows fluorination chemistry with $F_2$ gas with concentrations preferably equal to substantially more than, in particular very much higher than 25% by volume of elemental fluorine ($F_2$). In a applying the present fluorination process it is possible to perform chemistry with $F_2$ as it comes directly out of the $F_2$-electrolysis reactors (fluorine cells). A representative composition of fluorine gas produced by a fluorine cell is 97% $F_2$, up to 3% $CF_4$ (formed from damage of the electrodes), for example, traces of HF, $NO_2$, $OF_2$, $COF_2$, each % by volume and based on the total volume of the fluorine containing gas as 100% by volume. Regarding the scope of the present invention it is to be noted that, that for legal reason only but not for technical reason, there is a proviso that the starting compound, to be reacted with the fluorination gas, is only benzoic acid, and the fluorinated compound produced is only benzoic acid hypofluorite, and/or subsequently a fluorinated benzene, preferably the fluorinated benzene produced is only monofluorobenzene.

In the fluorination gas the elemental fluorine ($F_2$) may be diluted by an inert gas. The inert gas then constitutes the substantial difference (e.g., there may be only minor quantities of by-products (e.g., $CF_4$) of no more than about 5% by volume, preferably of no more than about 3% by volume, and only traces impurities (e.g., such like HF, $NO_2$, $OF_2$, $COF_2$), in the fluorination gas.

An inert gas is a gas that does not undergo chemical reactions under a set of given conditions. The noble gases often do not react with many substances and were historically referred to as the inert gases. Inert gases are used generally to avoid unwanted chemical reactions degrading a sample. These undesirable chemical reactions are often oxidation and hydrolysis reactions with the oxygen and moisture in air.

Typical inert gases are noble gases, and the very common inert gas nitrogen ($N_2$). The noble gases (historically also the inert gases; sometimes referred to as aerogens) make up a group of chemical elements with similar properties; under standard conditions, they are all odorless, colorless, monatomic gases with very low chemical reactivity. The six noble gases that occur naturally are helium (He), neon (Ne), argon (Ar), krypton (Kr), xenon (Xe), and the radioactive radon (Rn).

Purified argon and nitrogen gases are most commonly used as inert gases due to their high natural abundance (78.3% $N_2$, 1% Ar in air) and low relative cost. The preferred is nitrogen ($N_2$) as the inert gas for diluting the elemental fluorine ($F_2$) in the fluorination gas to the desired but still high concentration, as defined herein.

Preferred is a fluorination gas, wherein the elemental fluorine ($F_2$) is diluted by nitrogen ($N_2$). An example composition of a fluorination gas, using nitrogen ($N_2$) as the inert gas, is as follows (here as purified composition (fluorine-nitrogen gas mixture) as filled in a steel gas cylinder):

| Molecular Formula: $F_2$ Item | Molecular Weight: 38 Index |
|---|---|
| $F_2$ content (volume fraction)/$10^{-2}$ | 20 |
| $N_2$ content (volume fraction)/$10^{-2}$ | 80 |
| $O_2$ content (volume fraction)/$10^{-2}$ | ≤0.08 |
| $CF_4$ content (volume fraction)/$10^{-2}$ | ≤0.03 |
| HF content (volume fraction)/$10^{-2}$ | ≤0.50 |

Properties: melting point: −218° C., boiling point: −187° C., relative density (moisture = 1) 1.14 (−200° C.), soluble in water, relative density (air = 1) 1.70, saturated vapor pressure (kpa): 101.32 (−187° C.), critical pressure (MPA): 5.57.

The following two Figures (i.e. FIG. 1 and FIG. 2) illustrate the industrial options to use $F_2$ gas with little or even with no dilution with inert gas:

FIG. 1: Fluorination using a gas scrubber system.

Batch fluorination with elemental fluorine ($F_2$) gas, optionally highly concentrated $F_2$ gas in a counter-current system (the reservoir is containing the liquid raw material or optionally the raw material in an inert solvent). If highly concentrated $F_2$ is used together with some inert gas (e.g. 10% $N_2$) the pressure during the fluorination is kept at 5 bar (absolute) by a pressure valve. The inert gas together with (only) some HF leaves as purge gas during reaction.

Figure 2:
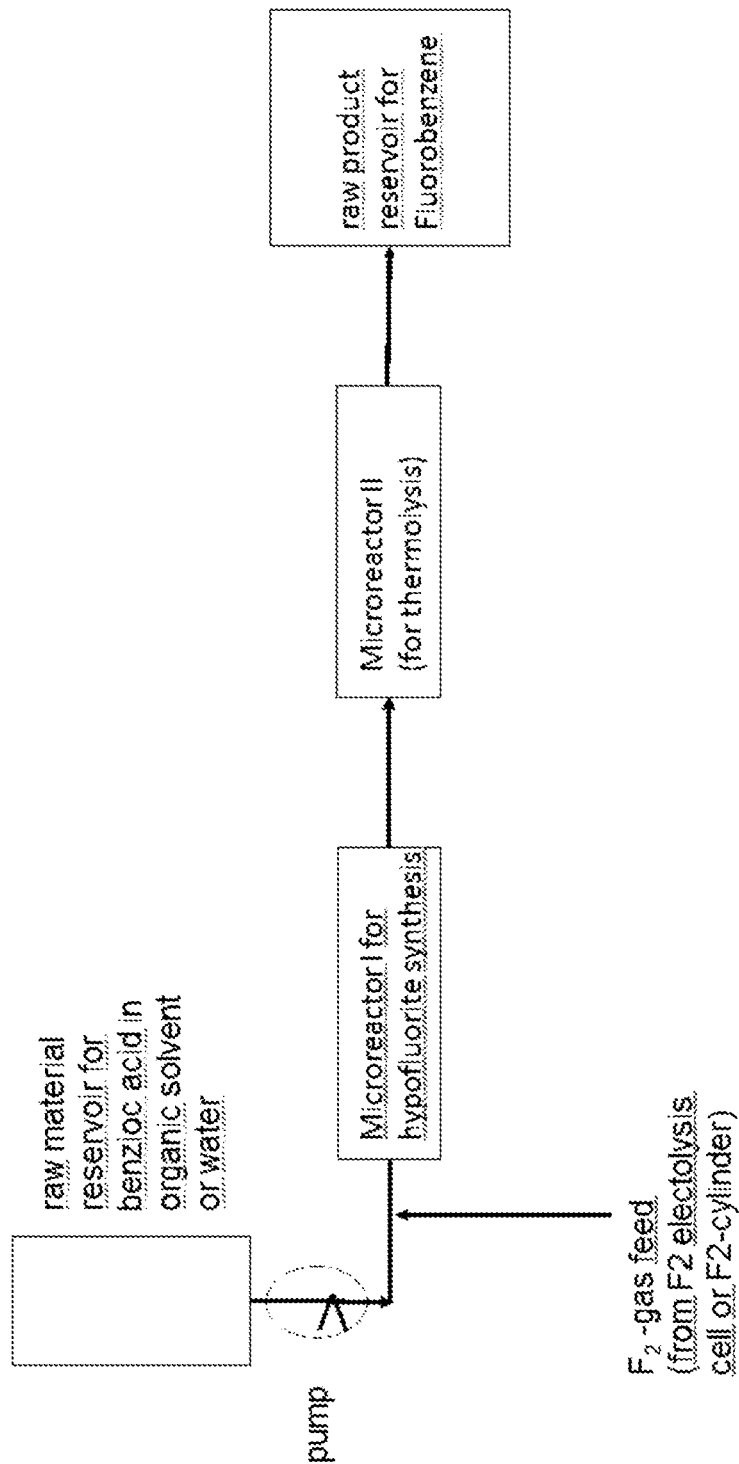
FIG. 2 shows continuous fluorination in a one or several microreactor (in series) system.

FIG. 2: Continuous fluorination in a one or several microreactor (in series) system.

The raw material reservoir still contains the equimolar formed HF. This can be subjected a batch or continuous distillation or if a solvent is present, after removal of the solvent and HF a re-crystallization for purification. Spray drying is another option depending on the product properties. A second or even more microreactor in series is just for the purpose of extending the residence time if needed.

Fluorination With Fluorination Gas Containing Elemental Fluorine in a High Concentration:

As shown in the examples, the direct fluorination using fluorine gas ($F_2$), e.g., in a step of fluorinating benzoic acid to obtain benzoic acid hypofluorite, can be performed already with a fluorination gas, based on the total fluorination gas composition as 100% by volume, comprising at least 20% by volume of elemental fluorine ($F_2$) and up to about 80% by volume of an inert gas, preferably nitrogen ($N_2$), for example, the composition of a fluorination gas, using nitrogen ($N_2$) as the inert gas, as escribed above as purified composition fluorine-nitrogen gas mixture as filled in a steel gas cylinder.

By the present invention it was found that the fluorination process according to the invention is already feasible with a fluorination gas, based on the total fluorination gas composition as 100% by volume, comprising at least 20% by volume of elemental fluorine ($F_2$), but for an industrial process undesirably low conversion rates of only about up to 30 to 45% are achieved.

Surprisingly it was also found that the use of inert gas in larger ratios of inert gas to elemental fluorine has disadvantages in terms of process controllability of the fluorination reaction, for example, in terms of effective mixing of the elemental fluorine with the liquid compound to be fluorinated, heat transfer control, e.g., poor heat exchange, and maintenance of desired reaction conditions in the microenvironments in the reaction mixture. These disadvantages equally apply in bed tower reactor (gas scrubber system) technology and in microbubble microreactor or comparable continuous flow technology. For example, in a coil reactor or microreactor, at high inert gas concentrations, e.g., low fluorine ($F_2$) concentrations, in addition to the poor heat exchange, there are also ineffective (reaction) zones with (inert) gas bubbles, which nullifies the advantages of using a coil reactor or a microreactor, and the same is observed in bed tower reactor (gas scrubber system) technology.

However, it was also found by the present invention that, based on the total fluorination gas composition as 100% by volume, increasing the concentration of elemental fluorine ($F_2$) in the fluorination gas to a higher concentration of greater than 20% by volume, e.g., preferably of greater than 25% by volume, more preferably of greater than 30% by volume or 40% by volume, and most preferably of greater than 50% by volume, while on the other hand decreasing the concentration of the inert gas, e.g., of the inert gas nitrogen ($N_2$), to a corresponding lower concentration of less than 80% by volume, e.g., preferably of less than 75% by volume, more preferably of less than 70% by volume or 60% by volume, and most preferably of less than 50% by volume, for an industrial process gradually increasing conversion rates of essentially above about 30 to 45%, e.g. conversion rates of more than 50% by volume, preferably of more than 60% by volume, or more than 70% by volume, or more than 70% by volume, even more preferably of more than 80% by volume, and most preferably of more than 90% by volume, can be achieved.

Without wishing to be bound to a theory, it is estimated that the inert gas used to dilute the reactivity of the strongly oxidant elemental fluorine ($F_2$), which is required for safety reasons when handling and transporting elemental fluorine ($F_2$) as described in the background above (e.g., in Europe mixtures of 95% by volume N2 (inert gas) with only 5% by volume $F_2$-gas, or in Asia, e.g., at least 80% by volume N2 (inert gas) with only up to 20% by volume $F_2$-gas) is jeopardizing the fluorination reaction, despite the fact that the elemental fluorine ($F_2$) contained in such a diluted fluorination gas still is strong oxidant.

Surprisingly, by the present invention it was found, that direct fluorination of compounds, a direct fluorination using fluorine gas ($F_2$), e.g., in a step of fluorinating benzoic acid to obtain benzoic acid hypofluorite, with even higher conversion rates than those obtained with the said conventional diluted fluorination gases can be achieved, if the elemental fluorine ($F_2$) is undiluted by inert gas, or elemental fluorine ($F_2$) is diluted by inert gas only to a concentration of greater than 50% by volume elemental fluorine ($F_2$) in the fluorination gas, based on the total fluorination gas composition as 100% by volume.

Therefore, it is particularly preferred by the present invention to provide a fluorination process for the manufacture or preparation of fluorobenzene, in particular monofluorobenzene, involving a step of direct fluorination, e.g., a step of fluorinating benzoic acid to obtain benzoic acid hypofluorite, using fluorine gas ($F_2$) as it comes directly out of a $F_2$-electrolysis reactor (fluorine cell).

A representative composition of fluorine gas produced by a fluorine cell is 97% $F_2$, up to 3% $CF_4$ (formed from damage of the electrodes), traces of HF, $NO_2$, $OF_2$, $COF_2$, each % by volume and based on the total volume of the fluorine containing gas as 100% by volume.

Purification of the fluorination gas as it is derived from a $F_2$-electrolysis reactor (fluorine cell), if desired, optionally is possible, to remove a part or all by-products and traces formed in the $F_2$-electrolysis reactor (fluorine cell), prior to its use as fluorination gas in the process of the present invention. However, in the process of the present invention such a partial or complete purification is not required, and the fluorination gas can be directly used, as it comes directly out of a $F_2$-electrolysis reactor (fluorine cell).

When employing a fluorination gas derived from a $F_2$-electrolysis reactor (fluorine cell), purified or unpurified, it may, if desired, optionally be diluted to some extent by an inert gas, preferably by nitrogen ($N_2$).

Hence, such a fluorination gas, purified or unpurified, as it is derived from a $F_2$-electrolysis reactor (fluorine cell), if desired, may optionally be diluted by up to about 45% by volume of inert gas, but preferably the fluorination gas is not diluted by inert gas to a concentration of elemental fluorine ($F_2$) in the fluorination gas of less 80% by volume, preferably of less than 85% by volume, more preferably of less than 90% by volume, based on the total fluorination gas composition as 100% by volume.

The difference of the sum of the elemental fluorine ($F_2$) and any inert gas in the fluorination gas to 100% by volume, if any difference, may be constituted by by-products (e.g., $CF_4$) and traces of HF, $NO_2$, $OF_2$, $COF_2$, formed from damage of the electrodes of the $F_2$-electrolysis reactor (fluorine cell). This applies generally to the % by volume values given herein above and herein below, if fluorine gas ($F_2$), as it comes directly out of a $F_2$-electrolysis reactor (fluorine cell) is used as the fluorination gas in the present invention.

Accordingly, in a preferred process of the invention the direct fluorination, e.g., the step of fluorinating benzoic acid to obtain benzoic acid hypofluorite, is carried out with a fluorination gas comprising about 80% by volume to 97±1% of elemental fluorine ($F_2$) and about 0% to 17±1% of inert gas, preferably of nitrogen ($N_2$), based on the total fluorination gas composition as 100% by volume.

In a further preferred process of the invention the direct fluorination, e.g., the step of fluorinating benzoic acid to obtain benzoic acid hypofluorite, is carried out with a fluorination gas comprising about 85% by volume to 97±1% of elemental fluorine ($F_2$) and about 0% to 12±1% of inert gas, preferably of nitrogen ($N_2$), based on the total fluorination gas composition as 100% by volume.

In a furthermore preferred process of the invention the direct fluorination, e.g., the step of fluorinating benzoic acid to obtain benzoic acid hypofluorite, is carried out with a fluorination gas comprising about 87% by volume to 97±1% of elemental fluorine ($F_2$) and about 0% to 10±1% of inert gas, preferably of nitrogen ($N_2$), based on the total fluorination gas composition as 100% by volume.

In another preferred process of the invention the direct fluorination, e.g., the step of fluorinating benzoic acid to obtain benzoic acid hypofluorite, is carried out with a fluorination gas comprising about 90% by volume to 97±1% of elemental fluorine ($F_2$) and about 0% to 7±1% of inert gas, preferably of nitrogen ($N_2$), based on the total fluorination gas composition as 100% by volume.

In still another preferred process of the invention the direct fluorination, e.g., the step of fluorinating benzoic acid to obtain benzoic acid hypofluorite, is carried out with a fluorination gas comprising about 95% by volume to 97±1% of elemental fluorine ($F_2$) and about 0% to 2±1% of inert gas, preferably of nitrogen ($N_2$), based on the total fluorination gas composition as 100% by volume.

It goes without saying that a person skilled in the art understands that within any of the given ranges any intermediate values and intermediate ranges can be selected, too.

Use of Fluorination Gas With High Concentration of Elemental Fluorine:

The invention also relates to a use of a fluorination gas, preferably wherein elemental fluorine ($F_2$) is present in a high concentration of substantially more than, in particular very much more than 15% by volume or in particular than 20% by volume of elemental fluorine ($F_2$), especially of equal to much higher than 25% by volume, i.e., at least 25% by volume, of elemental fluorine ($F_2$), preferably of equal to much higher than 35% by volume or in particular than 45% by volume, for the manufacture of benzoic acid hypofluorite, and/or subsequently a fluorinated benzene in a liquid medium comprising or consisting of a benzoic acid as starting compound, characterized in that the starting compound is benzoic acid, and the fluorinated compound produced is benzoic acid hypofluorite, and/or subsequently a fluorinated benzene, preferably monofluorobenzene.

In general, in one aspect the invention is also directed to the use of a fluorination gas, preferably wherein the elemental fluorine ($F_2$) is present in a high concentration, e.g., a use in a process for the manufacture of benzoic acid hypofluorite, and/or subsequently a fluorinated benzene according to the invention, wherein the elemental fluorine ($F_2$) is present in the fluorination gas in a high concentration of at least 25% by volume, preferably of at least 30% by volume, more preferably of at least 35% by volume, even more preferably of at least 45% by volume, each based on the total volume of the fluorination gas as 100% by volume.

Furthermore, in the said use, the elemental fluorine ($F_2$) can be present in the fluorination gas in a high concentration of at least 45% by volume, preferably of at least 50% by volume, more preferably of at least 60% by volume, even more preferably of at least 70% by volume, or of at least 80% by volume, each based on the total volume of the fluorination gas as 100% by volume.

In the said use for the manufacture of benzoic acid hypofluorite, and/or subsequently a fluorinated benzene, preferably monofluorobenzene, according to the invention, in an embodiment the elemental fluorine ($F_2$) is present in the fluorination gas in a high concentration within a range of from 15-100% by volume, preferably within a range of from 20-100% by volume, more preferably within a range of from 25-100% by volume, still more preferably within a range of from 30-100% by volume, even more preferably within a range of from 35-100% by volume, an still more preferred within a range of from 45-100% by volume, each based on the total volume of the fluorination gas as 100% by volume.

Furthermore, in the said use, the elemental fluorine ($F_2$) can be present in the fluorination gas in a high concentration within a range of from 45-100% by volume, preferably within a range of from 50-100% by volume, more preferably within a range of from 60-100% by volume, still more preferably within a range of from 70-100% by volume, even more preferably within a range of from 80-100% by volume, each based on the total volume of the fluorination gas as 100% by volume.

The Process of the Invention:

As briefly described in the Summary of the Invention, and defined in the claims and further detailed by the following description and examples herein, the invention is particularly directed to a process for the manufacture of benzoic acid hypofluorite, and/or subsequently a fluorinated benzene, involving a step of direct fluorination, e.g., a step of fluorinating benzoic acid to obtain benzoic acid hypofluorite, wherein the process comprises the steps of direct fluorination and decarboxlation as described herein after.

An embodiment of the invention relates to a process for the manufacture of a fluorinated benzene, preferably monofluorobenzene, wherein the process comprises the steps of:
 a) provision of a liquid medium comprising benzoic acid as starting compound;
 b) provision of a fluorination gas comprising or consisting of elemental fluorine ($F_2$), preferably wherein the fluorine is present in the fluorination gas in a high concentration of at least substantially more than, in particular very much more than 15% by volume (vol.-%), preferably equal to or more than 20% by volume (vol.-%);
 c) provision of a first reactor or reactor system, resistant to elemental fluorine ($F_2$) and hydrogen fluoride (HF);
 d) in a step of direct fluorination, passing the fluorination gas of b), in a reactor or reactor system of c), through the liquid medium of a) comprising the benzoic acid as starting compound, and thereby reacting the benzoic acid starting compound with the elemental fluorine ($F_2$) of the fluorination gas a) to substitute in the hydrogen atom in the benzoic acid carboxylic group for fluorine, and wherein the reaction is carried out at temperature of from about −30° C. to about +100° C. and a pressure of from about 1 bar absolute bar to about 10 bar absolute bar;
 e) withdrawing the benzoic acid hypofluorite formed in the direct fluorination step d) from the reactor or reactor system of c);

f) to obtain the benzoic acid hypofluorite, in situ or in isolated form; and g) subjecting the benzoic acid hypofluorite obtained in step f), in situ or in isolated form, in a second reactor or reactor system to decarboxylation, to thereby obtain the fluorinated benzene, preferably to obtain monofluorobenzene.

In the said process for the manufacture of benzoic acid hypofluorite, and/or subsequently a fluorinated benzene, preferably monofluorobenzene, according to the invention, in an embodiment the elemental fluorine ($F_2$) is present in the fluorination gas of b) in a high concentration of at least 25% by volume, preferably of at least 30% by volume, more preferably of at least 35% by volume, even more preferably of at least 45% by volume, each based on the total volume of the fluorination gas as 100% by volume.

In the said process for the manufacture of benzoic acid hypofluorite, and/or subsequently a fluorinated benzene, preferably monofluorobenzene, according to the invention, in an embodiment the fluorine ($F_2$) is present in the fluorination gas of b) in a high concentration within a range of from 15-100% by volume, preferably within a range of from 20-100% by volume, more preferably within a range of from 25-100% by volume, still more preferably within a range of from 30-100% by volume, even more preferably within a range of from 35-100% by volume, an still more preferred within a range of from 45-100% by volume, each based on the total volume of the fluorination gas as 100% by volume.

Batch Process:

The invention also may pertain to a process for the manufacture of benzoic acid hypofluorite, and/or subsequently a fluorinated benzene, preferably monofluorobenzene, wherein the process is a batchwise process, preferably wherein the batchwise process is carried out in a column reactor. Although, in the following reactor setting the process is described as a batch process, as preferred, for example, in case of high product concentrations, optionally the process can be performed in the said reactor setting also as a continuous process. In case of a continuous process in the said reactor setting, then, it goes without saying, the additional inlet(s) and outlet(s) are foreseen, for feeding the starting compound and withdrawing the product compound, respectively.

If the invention pertains to a batchwise process, preferably wherein the batchwise process is carried out in a column reactor, the process for the manufacture of benzoic acid hypofluorite, and/or subsequently a fluorinated benzene, preferably monofluorobenzene, according, most preferably the reaction is carried out in a (closed) column reactor (system), wherein the liquid medium of a) comprising or consisting of the starting compound benzoic acid is circulated in a loop, while the fluorination gas of b) comprising or consisting of elemental fluorine ($F_2$), optionally elemental fluorine ($F_2$) in a high concentration, is fed into the column reactor, and c) is passed through the liquid medium to react with the starting compound benzoic acid; preferably wherein the loop is operated with a circulation velocity of from about 1,500 l/h to about 5,000 l/h, more preferably of from about 3,500 l/h to about 4,500 l/h. In an example, the loop is operated with a circulation velocity of about 4,000 l/h.

If the invention pertains to a batchwise process, the process for the manufacture of benzoic acid hypofluorite, and/or subsequently a fluorinated benzene, preferably monofluorobenzene, according to the invention can be carried out such that the liquid medium of a) comprising or consisting of the starting compound benzoic acid is circulated in the column reactor in a turbulent stream or in laminar stream, preferably in a turbulent stream.

In general, the fluorination gas containing the elemental fluorine ($F_2$) is fed into the loop in accordance with the required stoichiometry for the targeted fluorinated product and fluorination degree, and adapted to the reaction rate.

The said process for the manufacture of benzoic acid hypofluorite, and/or subsequently a fluorinated benzene, preferably monofluorobenzene, according to the invention, may be performed, e.g., batchwise, wherein the column reactor is equipped with at least one of the following: at least one cooler (system), at least one liquid reservoir for the liquid medium of a) comprising or consisting of a starting compound benzoic acid, a pump (for pumping/circulating the liquid medium), one or more (nozzle) jets, preferably placed at the top of the column reactor, for spraying the circulating medium into the column reactor, one or more feeding inlets for introducing the fluorination gas of b) comprising or consisting of elemental fluorine ($F_2$), optionally elemental fluorine ($F_2$) in a high concentration, optionally one or more sieves, preferably two sieves, preferably the one or more sieves placed at the bottom of the column reactor, at least one gas outlet equipped with a pressure valve.

The pressure valve functions to keep the pressure, as required in the reaction, and to release any effluent gas, e.g. inert carrier gas contained in the fluorination gas, if applicable together with any hydrogen fluoride (HF) released from the reaction.

The said process for the manufacture of benzoic acid hypofluorite, and/or subsequently a fluorinated benzene, preferably monofluorobenzene, according to the invention, may be performed, e.g., batchwise, such that in the said process for the manufacture of benzoic acid hypofluorite, and/or subsequently a fluorinated benzene, preferably monofluorobenzene, the column reactor is a packed bed tower reactor, preferably a packed bed tower reactor which is packed with metal fillers.

The packed tower according to FIG. 1 can have a diameter of, e.g., 100 or 200 mm (depending on the circulating flow rate and scale) made out of high grade stainless steel (1.4571) and a length of, e.g., 3 meters for the 100 mm and, e.g., a length of 6 meters for the 200 mm diameter tower (latter if higher capacities are needed). The tower made out of Hastelloy is filled either with E-TFE or metal fillings each of, e.g., 10 mm diameter as available from Raschig (http://www.raschig.de/Fllkrper). The type of fillings is quite flexible, Raschigs Pall-Rings made out of Hastelloy were used in the trials disclosed hereunder, also E-TFE-fillings showed same performance, both not causing too much pressure reduction (pressure loss) while feeding $F_2$-gas in counter-current manner.

In the process for the manufacture of benzoic acid hypofluorite, and/or subsequently a fluorinated benzene, preferably monofluorobenzene, according to any of the embodiments of the invention, the reaction may be carried out with a counter-current flow of circulating liquid medium of a) comprising or consisting of the starting compound benzoic acid and the fluorination gas of b) fed into the column reactor and comprising or consisting of elemental fluorine ($F_2$), optionally elemental fluorine ($F_2$) in a high concentration.

Here, the invention comprises, for example, the following embodiments.

In one embodiment, a process for the manufacture of benzoic acid hypofluorite, and/or subsequently a fluorinated benzene according to the invention, wherein the reaction in step d) is carried out in a (closed) column reactor, wherein the liquid medium of a) comprising or consisting of the benzoic acid as the starting compound is circulated in a loop, while the fluorination gas of b) comprising or consisting of elemental fluorine ($F_2$), optionally elemental fluorine ($F_2$) in a high concentration, is fed into the column reactor of c) and in step d) is passed through the liquid medium to react with the starting compound benzoic acid; preferably wherein the loop is operated with a circulation velocity of from 1,500 l/h to 5,000 l/h, more preferably of from 3,500 l/h to 4,500 l/h.

In further embodiment, a process for the manufacture of benzoic acid hypofluorite, and/or subsequently a fluorinated benzene according to the invention, wherein the column reactor is equipped with at least one of the following:
  (i) at least one cooler (system), at least one liquid reservoir, with inlet and outlet for, and containing the liquid medium of a) comprising or consisting of benzoic acid as the starting compound;
  (ii) a pump for pumping and circulating the liquid medium of a);
  (iii) one or more (nozzle) jets, preferably wherein the one or more (nozzle) jets are placed at the top of the column reactor, for spraying the circulating medium of a) into the column reactor;
  (iv) one or more feeding inlets for introducing the fluorination gas of b) comprising or consisting of elemental fluorine ($F_2$), optionally elemental fluorine ($F_2$) in a high concentration, into the column reactor;
  (v) optionally one or more sieves, preferably two sieves, preferably the one or more sieves placed at the bottom of the column reactor;
  (vi) and at least one gas outlet equipped with a pressure valve, and at least one outlet for withdrawing the benzoic acid hypofluorite, for in situ or in isolated form, in step e).

In another embodiment, a process for the manufacture of benzoic acid hypofluorite, and/or subsequently a fluorinated benzene according to the invention, wherein column reactor is a packed bed tower reactor, preferably a packed bed tower reactor which is packed with fillers resistant to elemental fluorine ($F_2$) and hydrogen fluoride (HF), e.g. with Raschig fillers and/or metal fillers, more preferably wherein the packed bed tower reactor is a gas scrubber system (tower) which is packed with fillers resistant to elemental fluorine ($F_2$) and hydrogen fluoride (HF), e.g. Raschig fillers and/or metal fillers.

In still another embodiment, process for the manufacture of benzoic acid hypofluorite, and/or subsequently a fluorinated benzene according to the invention, wherein the reaction is carried out with a counter-current flow of the circulating liquid medium of a) comprising or consisting of the benzoic acid as starting compound and of the fluorination gas of b) fed into the column reactor and which fluorination gas of b) is comprising or consisting of elemental fluorine ($F_2$), optionally elemental fluorine ($F_2$) in a high concentration.

The batch process in the tower column described above, can also be performed, if desired, in a continuous manner. The person skilled in the field, e.g. in chemical engineering knows about appropriate means and its arrangement necessary to continuously feed in new starting compound and fluorination gas in the required amounts in a certain reaction time period to compensate for the starting compound converted into the fluorinated compound, which fluorinated compound is withdrawn from the reaction in a certain time period when performing the reaction continuously.

Microreactor Process:

The invention also may pertain to a process for the manufacture of benzoic acid hypofluorite, and/or subsequently a fluorinated benzene, preferably monofluorobenzene, according to any of the preceding claims, wherein the process is a continuous process, preferably wherein the continuous process is carried out in a microreactor.

In general, the fluorination gas containing the elemental fluorine ($F_2$) is fed into the microreactor in accordance with the required stoichiometry (sometimes with a slight excess) for the targeted fluorinated product and fluorination degree, and adapted to the reaction rate.

The invention may employ more than a single microreactor, i.e., the invention may employ two, three, four, five or more microreactors, for either extending the capacity or residence time, for example, to up to ten microreactors in parallel or four microreactors in series. If more than a single microreactor is employed, then the plurality of microreactors can be arranged either sequentially or in parallel, and if three or more microreactors are employed, these may be arranged sequentially, in parallel or both. See FIG. 2.

The invention is also very advantageous, in one embodiment wherein the direct fluorination of the invention, e.g., the step of fluorinating benzoic acid to obtain benzoic acid hypofluorite, optionally is performed in a continuous flow reactor system, or preferably in a microreactor system.

In an preferred embodiment the invention relates to a process for the manufacture of a fluorinated compound according to the invention, wherein the reaction is carried out in at least one step as a continuous processes, wherein the continuous process is performed in at least one continuous flow reactor with upper lateral dimensions of about ≤5 mm, or of about ≤4 mm,
  preferably in at least one microreactor;
  more preferably wherein of the said steps at least the step of a fluorination reaction is a continuous process in at least one microreactor under one or more of the following conditions:
    flow rate: of from about 10 ml/h up to about 400 l/h;
    temperature: of from about 30° C. up to about 150° C.;
    pressure: of from about 4 bar up to about 50 bar;
    residence time: of from about 1 second, preferably from about 1 minute, up to about 60 minutes.

In another preferred embodiment the invention relates to such a process of preparing a compound according to the invention, wherein at least one of the said continuous flow reactors, preferably at least one of the microreactors, independently is a SiC-continuous flow reactor, preferably independently is a SiC-microreactor.

The Continuous Flow Reactors and Microreactors:

In addition to the above, according to one aspect of the invention, also a plant engineering invention is provided, as used in the process invention and described herein, pertaining to the optional, and in some embodiments of the process invention, the process even preferred implementation in microreactors.

As to the term "microreactor": A "microreactor" or "microstructured reactor" or "microchannel reactor", in one embodiment of the invention, is a device in which chemical reactions take place in a confinement with typical lateral dimensions of about ≤1 mm; an example of a typical form of such confinement are microchannels. Generally, in the context of the invention, the term "microreactor": A "microreactor" or "microstructured reactor" or "microchannel reactor", denotes a device in which chemical reactions take place in a confinement with typical lateral dimensions of about ≤5 mm.

Microreactors are studied in the field of micro process engineering, together with other devices (such as micro heat exchangers) in which physical processes occur. The microreactor is usually a continuous flow reactor (contrast with/to a batch reactor). Microreactors offer many advantages over conventional scale reactors, including vast improvements in energy efficiency, reaction speed and yield, safety, reliability, scalability, on-site/on-demand production, and a much finer degree of process control.

Microreactors are used in "flow chemistry" to perform chemical reactions.

In flow chemistry, wherein often microreactors are used, a chemical reaction is run in a continuously flowing stream rather than in batch production. Batch production is a technique used in manufacturing, in which the object in question is created stage by stage over a series of workstations, and different batches of products are made. Together with job production (one-off production) and mass production (flow production or continuous production) it is one of the three main production methods. In contrast, in flow chemistry the chemical reaction is run in a continuously flowing stream, wherein pumps move fluid into a tube, and where tubes join one another, the fluids contact one another. If these fluids are reactive, a reaction takes place. Flow chemistry is a well-established technique for use at a large scale when manufacturing large quantities of a given material. However, the term has only been coined recently for its application on a laboratory scale.

Continuous flow reactors, e.g. such as used as microreactor, are typically tube like and manufactured from non-reactive materials, such known in the prior art and depending on the specific purpose and nature of possibly aggressive agents and/or reactants. Mixing methods include diffusion alone, e.g. if the diameter of the reactor is narrow, e.g. <1 mm, such as in microreactors, and static mixers. Continuous flow reactors allow good control over reaction conditions including heat transfer, time and mixing. The residence time of the reagents in the reactor, i.e. the amount of time that the reaction is heated or cooled, is calculated from the volume of the reactor and the flow rate through it: Residence time=Reactor Volume/Flow Rate. Therefore, to achieve a longer residence time, reagents can be pumped more slowly, just a larger volume reactor can be used and/or even several microreactors can be placed in series, optionally just having some cylinders in between for increasing residence time if necessary for completion of reaction steps. In this later case, cyclones after each microreactor help to let escape any gas formed during reaction, e.g. HF formed in the in the (first) fluorination step HF or $CO_2$ formed in the (second) decarboxylation step, and to positively influence the reaction performance. Production rates can vary from milliliters per minute to liters per hour.

Some examples of flow reactors are spinning disk reactors (Colin Ramshaw); spinning tube reactors; multi-cell flow reactors; oscillatory flow reactors; microreactors; hex reactors; and aspirator reactors. In an aspirator reactor a pump propels one reagent, which causes a reactant to be sucked in. Also to be mentioned are plug flow reactors and tubular flow reactors.

In the present invention, in one embodiment it is particularly preferred to employ a microreactor.

In the use and processes according to the invention in a preferred embodiment the invention is using a microreactor. But it is to be noted in a more general embodiment of the invention, apart from the said preferred embodiment of the invention that is using a microreactor, any other, e.g. preferentially pipe-like, continuous flow reactor with upper lateral dimensions of up to about 1 cm, and as defined herein, can be employed. Thus, such a continuous flow reactor preferably with upper lateral dimensions of up to about ≤5 mm, or of about ≤4 mm, refers to a preferred embodiment of the invention, e.g. preferably to a microreactor. Continuously operated series of STRs is another option, but less preferred than using a microreactor.

In the before said embodiments of the invention, the minimal lateral dimensions of the, e.g. preferentially pipe-like, continuous flow reactor can be about >5 mm; but is usually not exceeding about 1 cm. Thus, the lateral dimensions of the, e.g. preferentially pipe-like, continuous flow reactor can be in the range of from about >5 mm up to about 1 cm, and can be of any value therein between. For example, the lateral dimensions of the, e.g. preferentially pipe-like, continuous flow reactor can be about 5.1 mm, about 5.5 mm, about 6 mm, about 6.5 mm, about 7 mm, about 7.5 mm, about 8 mm, about 8.5 mm, about 9 mm, about 9.5 mm, and about 10 mm, or can be can be of any value intermediate between the said values.

In the before said embodiments of the invention using a microreactor preferentially the minimal lateral dimensions of the microreactor can be at least about 0.25 mm, and preferably at least about 0.5 mm; but the maximum lateral dimensions of the microreactor does not exceed about ≤5 mm. Thus, the lateral dimensions of the, e.g. preferential microreactor can be in the range of from about 0.25 mm up to about ≤5 mm, and preferably from about 0.5 mm up to about ≤5 mm, and can be of any value therein between. For example, the lateral dimensions of the preferential microreactor can be about 0.25 mm, about 0.3 mm, about 0.35 mm, about 0.4 mm, about 0.45 mm, and about 5 mm, or can be of any value intermediate between the said values.

As stated here before in the embodiments of the invention in its broadest meaning is employing, preferentially pipe-like, continuous flow reactor with upper lateral dimensions of up to about 1 cm. Such continuous flow reactor, for example is a plug flow reactor (PFR).

The plug flow reactor (PFR), sometimes called continuous tubular reactor, CTR, or piston flow reactors, is a reactor used to perform and describe chemical reactions in continuous, flowing systems of cylindrical geometry. The PFR reactor model is used to predict the behavior of chemical reactors of such design, so that key reactor variables, such as the dimensions of the reactor, can be estimated.

Fluid going through a PFR may be modeled as flowing through the reactor as a series of infinitely thin coherent "plugs", each with a uniform composition, traveling in the axial direction of the reactor, with each plug having a different composition from the ones before and after it. The key assumption is that as a plug flows through a PFR, the fluid is perfectly mixed in the radial direction (i.e. in the lateral direction) but not in the axial direction (forwards or backwards).

Accordingly, the terms used herein to define the reactor type used in the context of the invention such like "continuous flow reactor", "plug flow reactor", "tubular reactor", "continuous flow reactor system", "plug flow reactor system", "tubular reactor system", "continuous flow system", "plug flow system", "tubular system" are synonymous to each other and interchangeably by each other.

The reactor or system may be arranged as a multitude of tubes, which may be, for example, linear, looped, meandering, circled, coiled, or combinations thereof. If coiled, for example, then the reactor or system is also called "coiled reactor" or "coiled system".

In the radial direction, i.e. in the lateral direction, such reactor or system may have an inner diameter or an inner cross-section dimension (i.e. radial dimension or lateral dimension, respectively) of up to about 1 cm. Thus, in an embodiment the lateral dimension of the reactor or system may be in the range of from about 0.25 mm up to about 1 cm, preferably of from about 0.5 mm up to about 1 cm, and more preferably of from about 1 mm up to about 1 cm.

In further embodiments the lateral dimension of the reactor or system may be in the range of from about >5 mm to about 1 cm, or of from about 5.1 mm to about 1 cm.

If the lateral dimension at maximum of up to about ≤5 mm, or of up to about ≤4 mm, then the reactor is called "microreactor". Thus, in still further microreactor embodiments the lateral dimension of the reactor or system may be in the range of from about 0.25 mm up to about ≤5 mm, preferably of from about 0.5 mm up to about ≤5 mm, and more preferably of from about 1 mm up to about ≤5 mm; or the lateral dimension of the reactor or system may be in the range of from about 0.25 mm up to about ≤4 mm, preferably of from about 0.5 mm up to about ≤4 mm, and more preferably of from about 1 mm up to about ≤4 mm.

In case reactants are solid inert solvents may be used. Thus, if raw materials shall be used, then the said solid raw materials are dissolved in an inert solvent. A suitable solvent is e.g. acetonitrile, or fully or partially fluorinated alkanes like Pentafluorobutane (365 mfc), linear or cyclic partially or fully fluorinated ethers like $CF_3$—$CH_2$—$OCHF_2$ (E245) or Octafluorotetrahydrofuran. Often, if available or after a first synthesis, the product as such can also serve as inert solvent, if liquid under the conditions. The direct fluorination reaction, and/or the decarboxylation reaction, of the present invention can also be carried out in water, if the solid starting compound is soluble in water ($H_2O$).

In an alternative embodiment of the invention, it is also optionally desired to employ another continuous flow reactor than a microreactor, preferably if, for example, the (halogenation promoting, e.g. the halogenation or preferably the halogenation) catalyst composition used in the halogenation or fluorination tends to get viscous during reaction or is viscous already as a said catalyst as such. In such case, a continuous flow reactor, i.e. a device in which chemical reactions take place in a confinement with lower lateral dimensions of greater than that indicated above for a microreactor, i.e. of greater than about 1 mm, but wherein the upper lateral dimensions are about ≤4 mm. Accordingly, in this alternative embodiment of the invention, employing a continuous flow reactor, the term "continuous flow reactor" preferably denotes a device in which chemical reactions take place in a confinement with typical lateral dimensions of from about ≥1 mm up to about ≤4 mm. In such an embodiment of the invention it is particularly preferred to employ as a continuous flow reactor a plug flow reactor and/or a tubular flow reactor, with the said lateral dimensions. Also, in such an embodiment of the invention, as compared to the embodiment employing a microreactor, it is particularly preferred to employ higher flow rates in the continuous flow reactor, preferably in the plug flow reactor and/or a tubular flow reactor, with the said lateral dimensions. For example, such higher flow rates, are up to about 2 times higher, up to about 3 times higher, up to about 4 times higher, up to about 5 times higher, up to about 6 times higher, up to about 7 times higher, or any intermediate flow rate of from about ≥1 up to about ≤7 times higher, of from about ≥1 up to about ≤6 times higher, of from about ≥1 up to about ≤5 times higher, of from about ≥1 up to about ≤4 times higher, of from about ≥1 up to about ≤3 times higher, or of from about ≥1 up to about ≤2 times higher, each as compared to the typical flow rates indicated herein for a microreactor. Preferably, the said continuous flow reactor, more preferably the plug flow reactor and/or a tubular flow reactor, employed in this embodiment of the invention is configured with the construction materials as defined herein for the microreactors. For example, such construction materials are silicon carbide (SiC) and/or are alloys such as a highly corrosion resistant nickel-chromium-molybdenum-tungsten alloy, e.g. Hastelloy®, as described herein for the microreactors.

A very particular advantage of the present invention employing a microreactor, or a continuous flow reactor with the before said lateral dimensions, the number of separating steps can be reduced and simplified, and may be devoid of time and energy consuming, e.g. intermediate, distillation steps. Especially, it is a particular advantage of the present invention employing a microreactor, or a continuous flow reactor with the before said lateral dimensions, that for separating simply phase separation methods can be employed, and the non-consumed reaction components may be recycled into the process, or otherwise be used as a product itself, as applicable or desired.

In addition to the preferred embodiments of the present invention using a microreactor according to the invention, in addition or alternatively to using a microreactor, it is also possible to employ a plug flow reactor or a tubular flow reactor, respectively.

Plug flow reactor or tubular flow reactor, respectively, and their operation conditions, are well known to those skilled in the field.

Although the use of a continuous flow reactor with upper lateral dimensions of about ≤5 mm, or of about ≤4 mm, respectively, and in particular of a microreactor, is particularly preferred in the present invention, depending on the circumstances, it could be imagined that somebody dispenses with an microreactor, then of course with yield losses and higher residence time, higher temperature, and instead takes a plug flow reactor or turbulent flow reactor, respectively. However, this could have a potential advantage, taking note of the mentioned possibly disadvantageous yield losses, namely the advantage that the probability of possible blockages (tar particle formation by non-ideal driving style) could be reduced because the diameters of the tubes or channels of a plug flow reactor are greater than those of a microreactor.

The possibly allegeable disadvantage of this variant using a plug flow reactor or a tubular flow reactor, however, may also be seen only as subjective point of view, but on the other hand under certain process constraints in a region or at a production facility may still be appropriate, and loss of yields be considered of less importance or even being acceptable in view of other advantages or avoidance of constraints.

In the following, the invention is more particularly described in the context of using a microreactor. Preferentially, a microreactor used according to the invention is a ceramic continuous flow reactor, more preferably a SiC (silicon carbide) continuous flow reactor, and can be used for material production at a multi-to scale. Within integrated heat exchangers and SiC materials of construction, it gives optimal control of challenging flow chemistry application. The compact, modular construction of the flow production reactor enables, advantageously for: long term flexibility towards different process types; access to a range of production volumes (5 to 400 l/h); intensified chemical production where space is limited; unrivalled chemical compatibility and thermal control.

Ceramic (SiC) microreactors, are e.g. advantageously diffusion bonded 3M SiC reactors, especially braze and metal free, provide for excellent heat and mass transfer, superior chemical compatibility, of FDA certified materials of construction, or of other drug regulatory authority (e.g. EMA) certified materials of construction. Silicon carbide (SiC), also known as carborundum, is a containing silicon and carbon, and is well known to those skilled in the art. For example, synthetic SiC powder is been mass-produced and processed for many technical applications.

For example, in the embodiments of the invention the objects are achieved by a method in which at least one reaction step takes place in a microreactor. Particularly, in preferred embodiments of the invention the objects are achieved by a method in which at least one reaction step takes place in a microreactor that is comprising or is made of SiC ("SiC-microreactor"), or in a microreactor that is comprising or is made of an alloy, e.g. such as Hastelloy C, as it is each defined herein after in more detail.

Thus, without being limited to, for example, in an embodiment of the invention the microreactor suitable for, preferably for industrial, production an "SiC-microreactor" that is comprising or is made of SiC (silicon carbide; e.g. SiC as offered by Dow Corning as Type G1SiC or by Chemtrix MR555 Plantrix), e.g. providing a production capacity of from about 5 up to about 400 kg per hour; or without being limited to, for example, in another embodiment of the invention the microreactor suitable for industrial production is comprising or is made of Hastelloy C, as offered by Ehrfeld. Such microreactors are particularly suitable for the, preferably industrial, production of fluorinated products according to the invention.

In order to meet both the mechanical and chemical demands placed on production scale flow reactors, Plantrix modules are fabricated from 3M™ SiC (Grade C). Produced using the patented 3M (EP 1 637 271 B1 and foreign patents) diffusion bonding technology, the resulting monolithic reactors are hermetically sealed and are free from welding lines/joints and brazing agents. More technical information on the Chemtrix MR555 Plantrix can be found in the brochure "CHEMTRIX—Scalable Flow Chemistry—Technical Information Plantrix® MR555 Series," published by Chemtrix BV in 2017, which technical information is incorporated herein by reference in its entirety.

Apart from the before said example, in other embodiments of the invention, in general SiC from other manufactures, and as known to the skilled person, of course can be employed in the present invention.

Accordingly, in the present invention as microreactor also the Protrix® of by Chemtrix can be used. Protrix® is a modular, continuous flow reactor fabricated from 3M® silicon carbide, offering superior chemical resistance and heat transfer. In order to meet both the mechanical and chemical demands placed on flow reactors, Protrix® modules are fabricated from 3M® SiC (Grade C). Produced using the patented 3M (EP 1 637 271 B1 and foreign patents) diffusion bonding technology, the resulting monolithic reactors are hermetically sealed and are free from welding lines/joints and brazing agents. This fabrication technique is a production method that gives solid SiC reactors (thermal expansion coefficient=$4.1 \times 10^{-6} K^{-1}$).

Designed for flow rates ranging from 0.2 to 20 ml/min and pressures up to 25 bar, Protrix® allows the user to develop continuous flow processes at the lab-scale, later transitioning to Plantrix® MR555 (×340 scale factor) for material production. The Protrix® reactor is a unique flow reactor with the following advantages: diffusion bonded 3M® SiC modules with integrated heat exchangers that offer unrivaled thermal control and superior chemical resistance; safe employment of extreme reaction conditions on a g scale in a standard fumehood; efficient, flexible production in terms of number of reagent inputs, capacity or reaction time. The general specifications for the Protrix® flow reactors are summarised as follows; possible reaction types are, e.g. A+B→P1+Q (or C)→P, wherein the terms "A", "B" and "C" represent educts, "P" and "P1" products, and "Q" quencher; throughput (ml/min) of from about 0.2 up to about 20; channel dimensions (mm) of 1×1 (pre-heat and mixer zone), 1.4×1.4 (residence channel); reagent feeds of 1 to 3; module dimensions (width×height) (mm) of 110×260; frame dimensions (width×height×length) (mm) approximately 400×300× 250; number of modules/frame is one (minimum) up to four (max.). More technical information on the ChemtrixProtrix® reactor can be found in the brochure "CHEMTRIX— Scalable Flow Chemistry—Technical Information Protrix®," published by Chemtrix BV in 2017, which technical information is incorporated herein by reference in its entirety.

The Dow Corning as Type G1SiC microreactor, which is scalable for industrial production, and as well suitable for process development and small production can be characterized in terms of dimensions as follows: typical reactor size (length×width×height) of 88 cm×38 cm×72 cm; typical fluidic module size of 188 mm×162 mm. The features of the Dow Corning as Type G1SiC microreactor can be summarized as follows: outstanding mixing and heat exchange: patented HEART design; small internal volume; high residence time; highly flexible and multipurpose; high chemical durability which makes it suitable for high pH compounds and especially hydrofluoric acid; hybrid glass/SiC solution for construction material; seamless scale-up with other advanced-flow reactors. Typical specifications of the Dow Corning as Type G1SiC microreactor are as follows: flow rate of from about 30 ml/min up to about 200 ml/min; operating temperature in the range of from about −60° C. up to about 200° C., operating pressure up to about 18 barg ("barg" is a unit of gauge pressure, i.e. pressure in bars above ambient or atmospheric pressure); materials used are silicon carbide, PFA (perfluoroalkoxy alkanes), perfluoroelastomer; fluidic module of 10 ml internal volume; options: regulatory authority certifications, e.g. FDA or EMA, respectively. The reactor configuration of Dow Corning as Type G1SiC microreactor is characterized as multipurpose and configuration can be customized. Injection points may be added anywhere on the said reactor.

Hastelloy® C is an alloy represented by the formula NiCr21Mo14W, alternatively also known as "alloy 22" or "Hastelloy® C-22." The said alloy is well known as a corrosion resistant nickel-chromium-molybdenum-tungsten alloy and has excellent resistance to oxidizing reducing and mixed acids. The said alloy is used in flue gas desulphurization plants, in the chemical industry, environmental protection systems, waste incineration plants, sewage plants. Apart from the before said example, in other embodiments of the invention, in general nickel-chromium-molybdenum-tungsten alloy from other manufactures, and as known to the skilled person, of course can be employed in the present invention. A typical chemical composition (all in weight-%) of such nickel-chromium-molybdenum-tungsten alloy is, each percentage based on the total alloy composition as 100%: Ni (nickel) as the main component (balance) of at least about 51.0%, e.g. in a range of from about 51.0% to about 63.0%; Cr (chromium) in a range of from about 20.0 to about 22.5%, Mo (molybdenum) in a range of from about 12.5 to about 14.5%, W (tungsten or wolfram, respectively) in a range of from about 2.5 to about 3.5%; and Fe (iron) in an amount of up to about 6.0%, e.g. in a range of from about 1.0% to about 6.0%, preferably in a range of from about 1.5% to about 6.0%, more preferably in a range of from about 2.0% to about 6.0%. Optionally, the percentage based on the total alloy composition as 100%, Co (cobalt) can be present in the alloy in an amount of up to about 2.5%, e.g. in a range of from about 0.1% to about 2.5%. Optionally, the percentage based on the total alloy composition as 100%, V (vanadium) can be present in the alloy in an amount of up to about 0.35%, e.g. in a range of from about 0.1% to about 0.35%. Also, the percentage based on the total alloy composition as 100%, optionally low amounts (i.e. ≤0.1%) of other element traces, e.g. independently of C (carbon), Si (silicon), Mn (manganese), P (phosphor), and/or S (sulfur). In such case of low amounts (i.e. ≤0.1%) of other elements, the said elements e.g. of C (carbon), Si (silicon), Mn (manganese), P (phosphor), and/or S (sulfur), the percentage based on the total alloy composition as 100%, each independently can be present in an amount of up to about 0.1%, e.g. each independently in a range of from about 0.01 to about 0.1%, preferably each independently in an amount of up to about 0.08%, e.g. each independently in a range of from about 0.01 to about 0.08%. For example, said elements e.g. of C (carbon), Si (silicon), Mn (manganese), P (phosphor), and/or S (sulfur), the percentage based on the total alloy composition as 100%, each independently can be present in an amount of, each value as an about value: C≤0.01%, Si≤0.08%, Mn≤0.05%, P≤0.015%, S≤0.02%. Normally, no traceable amounts of any of the following elements are found in the alloy compositions indicated above: Nb (niobium), Ti (titanium), Al (aluminum), Cu (copper), N (nitrogen), and Ce (cerium).

Hastelloy® C-276 alloy was the first wrought, nickel-chromium-molybdenum material to alleviate concerns over welding (by virtue of extremely low carbon and silicon contents). As such, it was widely accepted in the chemical process and associated industries, and now has a 50-year-old track record of proven performance in a vast number of corrosive chemicals. Like other nickel alloys, it is ductile, easy to form and weld, and possesses exceptional resistance to stress corrosion cracking in chloride-bearing solutions (a form of degradation to which the austenitic stainless steels are prone). With its high chromium and molybdenum contents, it is able to withstand both oxidizing and non-oxidizing acids, and exhibits outstanding resistance to pitting and crevice attack in the presence of chlorides and other halides. The nominal composition in weight-% is, based on the total composition as 100%: Ni (nickel) 57% (balance); Co (cobalt) 2.5% (max.); Cr (chromium) 16%; Mo (molybdenum) 16%; Fe (iron) 5%; W (tungsten or wolfram, respectively) 4%; further components in lower amounts can be Mn (manganese) up to 1% (max.); V (vanadium) up to 0.35% (max.); Si (silicon) up to 0.08% (max.); C (carbon) 0.01 (max.); Cu (copper) up to 0.5% (max.).

In another embodiments of the invention, without being limited to, for example, the microreactor suitable for the said production, preferably for the said industrial production, is an SiC-microreactor that is comprising or is made only of SiC as the construction material (silicon carbide; e.g. SiC as offered by Dow Corning as Type G1SiC or by Chemtrix MR555 Plantrix), e.g. providing a production capacity of from about 5 up to about 400 kg per hour.

It is of course possible according to the invention to use one or more microreactors, preferably one or more SiC-microreactors, in the production, preferably in the industrial production, of the fluorinated products according to the invention. If more than one microreactor, preferably more than one SiC-microreactors, are used in the production, preferably in the industrial production, of the fluorinated products according to the invention, then these microreactors, preferably these SiC-microreactors, can be used in parallel and/or subsequent arrangements. For example, two, three, four, or more microreactors, preferably two, three, four, or more SiC-microreactors, can be used in parallel and/or subsequent arrangements.

For laboratory search, e.g. on applicable reaction and/or upscaling conditions, without being limited to, for example, as a microreactor the reactor type Plantrix of the company Chemtrix is suitable. Sometimes, if gaskets of a microreactor are made out of other material than HDPTFE, leakage might occur quite soon after short time of operation because of some swelling, so HDPTFE gaskets secure long operating time of microreactor and involved other equipment parts like settler and distillation columns.

For example, an industrial flow reactor ("IFR", e.g. Plantrix® MR555) comprises of SiC modules (e.g. 3M® SiC) housed within a (non-wetted) stainless steel frame, through which connection of feed lines and service media are made using standard Swagelok fittings. The process fluids are heated or cooled within the modules using integrated heat exchangers, when used in conjunction with a service medium (thermal fluid or steam), and reacted in zig-zag or double zig-zag, meso-channel structures that are designed to give plug flow and have a high heat exchange capacity. A basic IFR (e.g. Plantrix® MR555) system comprises of one SiC module (e.g. 3M® SiC), a mixer ("MRX") that affords access to A+B→P type reactions. Increasing the number of modules leads to increased reaction times and/or system productivity. The addition of a quench Q/C module extends reaction types to A+B→P1+Q (or C)→P and a blanking plate gives two temperature zones. Herein the terms "A", "B" and "C" represent educts, "P" and "P1" products, and "Q" quencher.

Typical dimensions of an industrial flow reactor ("IFR", e.g. Plantrix® MR555) are, for example: channel dimensions in (mm) of 4×4 ("MRX", mixer) and 5×5 (MRH-I/MRH-II; "MRH" denotes residence module); module dimensions (width×height) of 200 mm×555 mm; frame dimensions (width×height) of 322 mm×811 mm. A typical throughput of an industrial flow reactor ("IFR", e.g. Plantrix® MR555) is, for example, in the range of from about 50 l/h to about 400 l/h. in addition, depending on fluid properties and process conditions used, the throughput of an industrial flow reactor ("IFR", e.g. Plantrix® MR555), for example, can also be >400 l/h. The residence modules can be placed in series in order to deliver the required reaction volume or productivity. The number of modules that can be placed in series depends on the fluid properties and targeted flow rate.

Typical operating or process conditions of an industrial flow reactor ("IFR", e.g. Plantrix® MR555) are, for example: temperature range of from about −30° C. to about 200° C.; temperature difference (service−process)<70° C.; reagent feeds of 1 to 3; maximum operating pressure (service fluid) of about 5 bar at a temperature of about 200° C.; maximum operating pressure (process fluid) of about 25 bar at a temperature of about ≤200° C.

Further Aspects of the Invention:

In one aspect, the invention relates to a use of a fluorination gas, comprising or consisting of elemental fluorine ($F_2$), optionally wherein elemental fluorine ($F_2$) is present in a high concentration of substantially more than, in particular very much more than 15% by volume or in particular than 20% by volume of elemental fluorine ($F_2$), especially of equal to much higher than 25% by volume, i.e., at least 25% by volume, of elemental fluorine ($F_2$), preferably of equal to much higher than 35% by volume or in particular than 45% by volume, for the manufacture of a fluorinated benzene in a liquid medium comprising benzoic acid as starting compound; preferably wherein the elemental fluorine ($F_2$) is present in the fluorination gas of b) in a high concentration in a range of from 15-100% by volume, preferably within a range of from 20-100% by volume, more preferably within a range of from 25-100% by volume, still more preferably within a range of from 30-100% by volume, even more preferably within a range of from 35-100% by volume, an still more preferred within a range of from 45-100% by volume, each based on the total volume of the fluorination gas as 100% by volume; characterized in that the starting compound is benzoic acid, and the fluorinated compound produced is a benzoic acid hypofluorite, which benzoic acid hypofluorite optionally subsequently is decarboxylated to obtain a fluorinated benzene.

In a further aspect, the invention relates to a process for the manufacture of a benzoic acid hypofluorite by direct fluorination of a benzoic acid, wherein the process comprises the steps of a) to f) as defined above and in claim 1, to obtain the benzoic acid hypofluorite, in situ or in isolated form.

In particular, according to the present invention the said process for the manufacture of a benzoic acid hypofluorite, wherein the process is performed according to the process as defined above for the direct fluorination process based on the benzoic acid as the starting compound, and, for example, as defined in any of the claims 2 to 9 for the steps a) to f).

In a still a further aspect, the invention relates to a use of a benzoic acid hypofluorite obtained, in situ or in isolated form, by direct fluorination of a benzoic acid in a process comprising the steps of a) to f), as defined above, and, for example, as defined in claim 1, in the manufacture of a fluorinated benzene, preferably monofluorobenzene; in particular by decarboxylation a benzoic acid hypofluorite; preferably by photochemical decarboxylation, more preferably by photochemical decarboxylation by direct irradiation ($\lambda$>180 nm) or by light initiation in presence of a photosensitizer; and more preferably by photochemical decarboxylation by direct irradiation induced by a wavelength of $\lambda$>180 nm.

In the said process for the manufacture of a fluorinated benzene, preferably monofluorobenzene, according to the invention as described above, and for example in claims 1 to 9, in step g) the decarboxylation of benzoic acid hypofluorite is carried out by photochemical decarboxylation; more preferably by photochemical decarboxylation by direct irradiation ($\lambda$>180 nm) or by light initiation in presence of a photosensitizer; and most preferably by photochemical decarboxylation by direct irradiation induced by a wavelength of $\lambda$>180 nm.

Finally, the invention in one aspect also relates to a process for the manufacture of a fluorinated benzene, preferably monofluorobenzene, wherein a benzoic acid hypofluorite is converted into a fluorinated benzene by decarboxylation; in particular by photochemical decarboxylation; preferably by photochemical decarboxylation; more preferably by photochemical decarboxylation by direct irradiation ($\lambda$>180 nm) or by light initiation in presence of a photosensitizer; and most preferably by photochemical decarboxylation by direct irradiation induced by a wavelength of $\lambda$>180 nm.

The following examples are intended to further illustrate the invention without limiting its scope.

EXAMPLES

In the following examples a fluorobenzene was prepared from a benzoic acid hypofluorite obtained by direct fluorination with a fluorination gas, preferably with a fluorination gas with high concentration of elemental fluorine ($F_2$), according to this invention, and subsequent decarboxylation, and according to the reaction Schemes given above in the description.

Representative, example procedures are described hereinafter in the embodiment following examples.

The examples are carried out in a representative scale of 200 g benzoic acid as a starting compound. Experiments were carried out in the reaction time frames as given in the description above, to yield the product quantities and conversion rates given below in the examples. Quantities of benzoic acid as a starting compound and/or reaction times may be easily adapted to produce the fluorinated products in large-scale and/or industrial production, e.g., benzoic acid hypofluorite and/or subsequently of fluorinated benzene, preferably monofluorobenzene. Accordingly, adapting Quantities of benzoic acid as a starting compound and/or reaction times may be easily adapted to at least about 1 kg of benzoic acid as the starting material is fluorinated per hour, preferably at least about 1.5 kg of benzoic acid as the starting material is fluorinated (e.g., less than 10 hours, or even less than 5 hours), to yield benzoic acid hypofluorite, and/or subsequently a fluorinated benzene, preferably monofluorobenzene, with a conversion of at least 80%, in particular of at least 85%, preferably about at least 90%, more preferably about at least 95% conversion.

Example 1

Synthesis of benzoic acid hypofluorite in $CH_3CN$ as solvent.

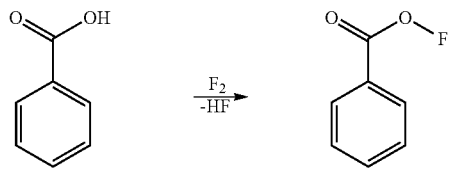 [SMILES: O=C(O)c1ccccc1 ; "F2" ; "-HF" ; O=C(OF)c1ccccc1]

In a 1 l counter-current system out of Hastelloy C4 like in the scheme described above, 200 g (1.64 mol) Benzoic acid is dissolved in 200 ml $CH_3CN$ (will not be fluorinated as benzoic acid is much more reactive) and circulated over the tower filled with (inert) plastic fillings. 68.4 g (1.80 mol) $F_2$-gas (20% in $N_2$) from a cylinder is fed at room temperature into the circulating mixture, formed HF is mainly (but not completely) leaving together with the $N_2$-stream over the top.

In the counter-current system the $F_2$-gas pressure (taken out of the pressure bottle), of course, was adjusted to compensate for the back pressure of the liquid medium level, and for pressing the $F_2$-gas through the liquid medium contained in the reactor. Accordingly, some back pressure through the liquid level is compensated by an $F_2$-gas pressure of no more than usually from about 2 bar (abs.) up to a maximum of about 3 bar (abs.).

Example 2

Pyrolysis of Benzoic Acid Hypofluorite.

100 g of the solution obtained in example 1 is pyrolyzed within 2 h at 200° C. in a 250 ml Roth autoclave made out of 1.4571, the autoclave contained 10 g Ni-fillings as catalyst). It was not tested if the reaction is also workable without nickel initiation. The pressure was kept at 20 bar by an automatic valve releasing overpressure created by formed $CO_2$. The resulting solution was washed with water, dried over $Na_2SO_4$ and subjected to a fine distillation over a distillation tower at atmospheric pressure over 5 h. 40.6 g fluorobenzene (92% of theory) were isolated at 85° C. as yellow liquid. As Acetonitrile and fluorobenzene have quite close boiling points, a very careful heating and distillation is essential.

Example 3

Pyrolysis of a Concentrated Solution of Benzoic Acid Hypofluorite.

100 g of the solution obtained in example 1 was concentrated by removing excess Acetonitrile at a rotavapor (plastic flask) at room temperature at 20 mbar. The remaining oil was pyrolyzed like described in example 2. The obtained yield in fluorobenzene was 42.8 g (97% of theory).

Example 4

Purification of Benzoic Acid Hypofluorite.

The solution obtained in example 1 was concentrated by removing excess acetonitrile at a rotavapor (plastic flask) at room temperature at 20 mbar like in example 3. The remaining oil now was fine distilled. 215.9 g benzoic acid hypofluorite was obtained at 51° C. transition temperature at 20 mbar (yield: 94% of theory).

Example 5

Pyrolysis of a Purified Benzoic Acid Hypofluorite Sample.

100 g (0.71 mol) of the purified benzoic acid hypofluorite out of example 4 was pyrolyzed like described in example 2. The obtained yield in fluorobenzene was 68.2 g (99% of theory).

Example 6

Synthesis of Benzoic Acid Hypofluorite in $H_2O$ as Solvent.

In a 1l countercurrent system out of Hastelloy C4 like in the scheme described above, 200 g (1.64 mol)benzoic acid is dissolved in 200 ml $H_2O$ and circulated over the tower filled with plastic fillings. 68.4 g (1.80 mol) $F_2$-gas (20% in $N_2$) from a cylinder is fed at room temperature into the circulating mixture, formed HF is kept in the water, the $N_2$-stream is leaving together with the little excess of $F_2$-gas over the top of the apparatus. After having finished the $F_2$-feed, the decarboxylation is done as described in example 7.

Example 7

Decarboxylation of Benzoic Acid Hypofluorite in $H_2O$.

100 g of the mixture as prepared in example 6 is transferred to a 250 ml Roth autoclave made out of 1.4571 high grade stainless steel containing Ni-fillings and heated to 200° C. for 2 h. The pressure was kept at 20 bar by an automatic valve releasing overpressure created by formed $CO_2$. After cooling down the resulting mixture is extracted with $CH_2Cl_2$ to obtain 40.1 g (91% of theory) fluorobenzene of 99% purity (GC) after removing the $CH_2C_{12}$ (together still with some little HF) by distillation.

Example 8

Photochemical Induced Decarboxylation.

The mixture obtained in example 6 was filtered to remove (little) particles and filled into a photoreactor equipped with a TQ 718 Hg high pressure lamp in a double wall quarz tube. The outer quarz tube which is in contact with the reaction media is covered with a FEP shrinking pipe (see https://www.polyfluor.nl/produkte/schrumpfschlauche/fep-schrumpfschlauche/) to avoid fluoride corrosion. The lamp itself (inside the double wall) was cooled by a flow of compressed air, the outer sphere of the photoreactor is made out of PE and has a double jacket and which is cooled with water so that the total reactor content is kept at or below 40° C. A very slow flow of $N_2$-gas was fed through the solution and was leaving over a bubble counter. The solution was now irradiated for 1 h at atmospheric pressure and in a temperature range between 30 and 40° C.; $CO_2$ evolution could be recognized at the bubble counter (observed after stopping the $N_2$-gas feed from time to time). The resulting mixture is extracted with $CH_2Cl_2$ to obtain 140.2 g (89% of theory) fluorobenzene of 99.2% purity (GC) after removing the $CH_2Cl_2$ (together still with some HF) by distillation.

Example 9

Continuous Photochemical Induced Decarboxylation in a Coil Reactor (FEP Pipe).

The mixture obtained on example 1 is fed at 2 bar abs. continuously with 100 ml/h through an FEP pipe of 5 mm diameter (see https://www.polyfluor.nl/de/produkte/-fluorkunststoff-schlauche/fep-schlauche/) and 1 m length and forms a coil. The irradiation was done by putting the coil into a RayonettRPR-100 irradiation reactor (supplier: "The Southern New England Ultraviolet Company") equipped with 254 nm lamps. The composition after having passed the 1 m FEP pipe showed a conversion of 82% and a selectivity to fluorobenzene of 97%.

Example 10

Continuous Hypofluorite Preparation and Decarboxylation in Microreactor System.

Scheme for a microreactor system for first and second step is shown in FIG. 2.

In Scheme 2, the first microreactor I is made out of stainless steel or SiC, and the microreactor II is made out of nickel.

The mixture obtained in example 1 is fed continuously with 250 ml/h, and a corresponding amount $F_2$-gas (20% in $N_2$) per hour from a cylinder, through a 27 ml microreactor from Chemtrix kept with cooling at 30° C. The microreactor I leaving material showed a conversion of 98% to benzoic acid hypofluorite. Afterwards the flow enters the second microreactor II of same volume made out of nickel and heated to 200° C. For microreactor II, Innosyn BV (Geelen, Netherlands) was chosen as supplier. All the material coming out of microreactor 2 was collected in a stainless steel cylinder (reservoir) and carefully distilled at room temperature to yield 83% fluorobenzene.

Example 11

Continuous Hypofluorite Preparation in Microreactor Combined With Continuous Decarboxylation in Coil Reactor.

Example 10 was repeated, but the second microreactor was replaced by the FEP coil reactor as in example 9. At pressure of 2 bar abs. the microreactor I leaving mixture enters the FEP coil put into a Southern New England Ultraviolet Company's Rayonett with 254 nm lamps. The conversion of benzoic acid was quantitative, and the isolated yield of fluorobenzene was 87%.

Example 12

Experiment done like example 10, but in water as solvent. After cooling down fluorobenzene separated as second phase from a water phase containing the majority of the HF. The yield of fluorobenzene was 93%.

Example 13

Experiment done like example 11, but in water as solvent. After cooling down fluorobenzene also separated as second phase from a water phase containing the majority of the HF. The yield of fluorobenzene was 97%.

What is claimed is:

1. A process for the manufacture of a fluorinated benzene, wherein the process comprises a plurality of steps of:
   a) provision of a liquid medium comprising benzoic acid as starting compound;
   b) provision of a fluorination gas comprising elemental fluorine, wherein the fluorine is present in the fluorination gas in a concentration equal to or more than 20% by volume;
   c) provision of a first reactor or reactor system, resistant to elemental fluorine and hydrogen fluoride;
   d) in a step of direct fluorination, passing the fluorination gas of b), in a reactor or reactor system of c), through the liquid medium of a) comprising the benzoic acid as starting compound, and thereby reacting the benzoic acid starting compound with the elemental fluorine of the fluorination gas a) to substitute in the hydrogen atom in the benzoic acid carboxlyic group for fluorine, and wherein the reaction is carried out at temperature of from about −30° C. to about +100° C. and a pressure of from about 1 bar absolute to about 10 bar absolute bar;
   e) withdrawing the benzoic acid hypofluorite formed in the direct fluorination step d) from the reactor or reactor system of c);
   f) to obtain the benzoic acid hypofluorite, in situ or in isolated form; and
   g) subjecting the benzoic acid hypofluorite obtained in step f), in situ or in isolated form, in a second reactor or reactor system to decarboxylation, to thereby obtain the fluorinated benzene.

2. The process for the manufacture of a fluorinated a fluorinated benzene according to claim 1, wherein the elemental fluorine is present in the fluorination gas of b) in a concentration of at least 25% by volume based on the total volume of the fluorination gas as 100% by volume.

3. The process for the manufacture of a fluorinated benzene according to claim 2, wherein the elemental fluorine is present in the fluorination gas of b) in a concentration within a range from 30-100% by volume based on the total volume of the fluorination gas as 100% by volume.

4. The process for the manufacture of a fluorinated benzene according to claim 1, wherein the reaction in step d) is carried out in a column reactor, wherein the liquid medium of a) comprising the benzoic acid as the starting compound is circulated in a loop, while the fluorination gas of b) comprising elemental fluorine ($F_2$), is fed into the column reactor of c) and in step d) is passed through the liquid medium to react with the starting compound benzoic acid wherein the loop is operated with a circulation velocity of from 1,500 l/h to 5,000 l/h.

5. The process for the manufacture of a fluorinated benzene according to claim 4, wherein the column reactor is equipped with at least one of the following:
   (i) at least one cooler, at least one liquid reservoir, with inlet and outlet for, and containing the liquid medium of a) comprising benzoic acid as the starting compound;
   (ii) a pump for pumping and circulating the liquid medium of a);
   (iii) one or more jets placed at the top of the column reactor, for spraying the circulating medium of a) into the column reactor;
   (iv) one or more feeding inlets for introducing the fluorination gas of b) comprising elemental fluorine ($F_2$) into the column reactor;
   (v) one or more sieves placed at the bottom of the column reactor; and
   (vi) at least one gas outlet equipped with a pressure valve, and at least one outlet for withdrawing the benzoic acid hypofluorite, for in situ or in isolated form, in step e).

6. The process for the manufacture of a fluorinated benzene according to claim 4, wherein column reactor is a packed bed tower reactor which is packed with fillers resistant to elemental fluorine and hydrogen fluoride.

7. The process for the manufacture of a fluorinated benzene according to claim 4, wherein the reaction is carried out with a counter-current flow of the circulating liquid medium of a) comprising the benzoic acid as starting compound and of the fluorination gas of b) fed into the column reactor and which fluorination gas of b) is comprising elemental fluorine ($F_2$).

8. The process for the manufacture of a fluorinated benzene according to claim 1, wherein the reaction is carried out in at least one step as a continuous process, wherein the continuous process is performed
   in at least one microreactor;
   wherein of the said steps at least the step of a fluorination reaction is a continuous process in at least one microreactor under one or more of the following conditions:
   flow rate: of from about 10 ml/h up to about 400 l/h;
   temperature: of from about 30° C. up to about 150° C.;
   pressure: of from about 4 bar up to about 50 bar;
   residence time: of from about 1 second up to about 60 minutes.

9. The process of preparing a fluorinated benzene according to claim 8, wherein at least one of the microreactors, independently is a SiC-microreactor.

10. A process for the manufacture of a benzoic acid hypofluorite by direct fluorination of a benzoic acid, wherein the process comprises a plurality of steps of a) to f), to obtain the benzoic acid hypofluorite, in situ or in isolated form; wherein the steps of a) to f) comprises:

a) provision of a liquid medium comprising benzoic acid as starting compound;

b) provision of a fluorination gas comprising elemental fluorine wherein the fluorine is present in the fluorination gas in a concentration equal to or more than 20% by volume;

c) provision of a first reactor or reactor system, resistant to elemental fluorine and hydrogen fluoride;

d) in a step of direct fluorination, passing the fluorination gas of b), in a reactor or reactor system of c), through the liquid medium of a) comprising the benzoic acid as starting compound, and thereby reacting the benzoic acid starting compound with the elemental fluorine of the fluorination gas a) to substitute in the hydrogen atom in the benzoic acid carboxlylic group for fluorine, and wherein the reaction is carried out at temperature of from about −30° C. to about +100° C. and a pressure of from about 1 bar absolute to about 10 bar absolute bar;

e) withdrawing the benzoic acid hypofluorite formed in the direct fluorination step d) from the reactor or reactor system of c); and f) to obtain the benzoic acid hypofluorite, in situ or in isolated form.

11. The process for the manufacture of a benzoic acid hypofluorite according to claim 10, wherein the elemental fluorine is present in the fluorination gas of b) in a concentration of at least 25% by volume based on the total volume of the fluorination gas as 100% by volume.

12. The process for the manufacture of a fluorinated benzene, according to claim 1, wherein in step g) the decarboxylation of benzoic acid hypofluorite is carried out by photochemical decarboxylation by direct irradiation induced by a wavelength of $\lambda > 180$ nm.

13. The process for the manufacture of a fluorinated benzene according to claim 2, wherein the elemental fluorine is present in the fluorination gas of b) in a concentration of at least 35% by volume based on the total volume of the fluorination gas as 100% by volume.

14. The process for the manufacture of a fluorinated benzene according to claim 13, wherein the elemental fluorine is present in the fluorination gas of b) in a concentration of at least 45% by volume based on the total volume of the fluorination gas as 100% by volume.

15. The process for the manufacture of a fluorinated benzene according to claim 4, wherein the loop is operated with a circulation velocity of from 3,500 l/h to 4,500 l/h.

16. The process for the manufacture of a fluorinated benzene according to claim 6, wherein the packed bed tower reactor is packed with Raschig fillers or metal fillers.

17. The process for the manufacture of a fluorinated benzene according to claim 6, wherein the packed bed tower reactor is a gas scrubber system.

18. The process for the manufacture of a fluorinated benzene according to claim 11, wherein the elemental fluorine is present in the fluorination gas of b) in a concentration of at least 35% by volume based on the total volume of the fluorination gas as 100% by volume.

19. The process for the manufacture of a fluorinated benzene according to claim 18, wherein the elemental fluorine is present in the fluorination gas of b) in a concentration of at least 45% by volume based on the total volume of the fluorination gas as 100% by volume.

* * * * *